US007065451B2

(12) United States Patent
Garner et al.

(10) Patent No.: US 7,065,451 B2
(45) Date of Patent: Jun. 20, 2006

(54) COMPUTER-BASED METHOD FOR CREATING COLLECTIONS OF SEQUENCES FROM A DATASET OF SEQUENCE IDENTIFIERS CORRESPONDING TO NATURAL COMPLEX BIOPOLYMER SEQUENCES AND LINKED TO CORRESPONDING ANNOTATIONS

(75) Inventors: Harold R. Garner, Flower Mound, TX (US); Amit Kulkarni, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 698 days.

(21) Appl. No.: 09/865,090

(22) Filed: May 24, 2001

(65) Prior Publication Data

US 2003/0033290 A1    Feb. 13, 2003

(51) Int. Cl.
*G06F 19/00* (2006.01)
*G06F 17/30* (2006.01)
*G05B 15/00* (2006.01)

(52) U.S. Cl. ............................... 702/20; 700/1; 707/3
(58) Field of Classification Search ............... 707/2–7, 707/101; 435/6, 69.1, 89, 91.4, 91.2; 702/19, 702/20; 703/11
See application file for complete search history.

(56) References Cited

U.S. PATENT DOCUMENTS

| | | | |
|---|---|---|---|
| 5,571,639 A * | 11/1996 | Hubbell et al. ................. 430/5 |
| 5,940,825 A * | 8/1999 | Castelli et al. ................. 707/6 |
| 6,221,600 B1 * | 4/2001 | MacLeod et al. ............... 435/6 |
| 6,303,297 B1 * | 10/2001 | Lincoln et al. ................. 435/6 |
| 6,355,450 B1 * | 3/2002 | Fleischmann et al. ..... 435/69.1 |
| 6,421,613 B1 * | 7/2002 | Nadimpalli et al. .......... 702/20 |
| 6,470,277 B1 * | 10/2002 | Chin et al. .................... 702/19 |
| 6,472,173 B1 * | 10/2002 | Ford et al. .................. 435/69.1 |
| 6,500,938 B1 * | 12/2002 | Au-Young et al. .......... 536/23.1 |
| 6,553,317 B1 * | 4/2003 | Lincoln et al. ............... 702/20 |
| 2002/0081603 A1 * | 6/2002 | Wolffe et al. .................. 435/6 |
| 2002/0194173 A1 * | 12/2002 | Bjornson et al. ............... 707/4 |
| 2003/0082572 A1 * | 5/2003 | Spier et al. ..................... 435/6 |

OTHER PUBLICATIONS

Hennig et al, A data-analysis pipeline for large-scale gene expression enalysis, 2000, ACM, pp. 165-173.*
King et al., Genome sacle prediction of protein functional class from sequence using data mining, 2000, ACM, pp. 384-389.*
Wang et al., Combinatorial pattern discovery for scientific data: Some preliminary results, May 1994, ACM, pp. 115-125.*
thomsonhc.com/pdrel/librarian/PFDefaultActionld/pdrcommon.Stedmans, Stedman's Medical Dictionary 27th Edition website, searching term "syngeneic" downloaded Aug. 11, 2005.*
Kulkarni et al. ARROGANT: an application to manipulate large gene collections. Bioinformatics vol. 18, No. 11, pp. 1410-1417 (2002).*

* cited by examiner

*Primary Examiner*—John S. Brusca
(74) *Attorney, Agent, or Firm*—Richard Aron Osman

(57) ABSTRACT

The invention relates to computer-based systems and methods for the design, comparison and analysis of genetic and proteomic databases. In a particular embodiment, the recited systems and methods have been implemented in a computer tool called ARROGANT. ARROGANT, in the analysis mode, is a comprehensive tool for providing annotation to large gene and protein collections. ARROGANT takes in a large collection of sequence identifiers and associates it with other information collected from many sources like sequence annotations, pathways, homology, polymorphisms, artifacts, etc. The simultaneous annotation for a large assembly of genes makes the collection of genomic/EST sequences truly informative.

21 Claims, 30 Drawing Sheets

FIG. 6

| Record | Accession No | Definition | Organism |
|---|---|---|---|
| 1 ☐ | A32415 | H.sapiens PAI-2 cDNA in pDBP1. | Homo sapiens |
| 2 ☐ | AA062310 | ml64f06.r1 Stratagene mouse kidney (#937315) Mus musculus cDNA clone IMAGE:516803 5' similar to WP:C40H1.6 CE00114 :, mRNA sequence. | Mus musculus |
| 3 ☐ | AA073008 | mm94c09.r1 Stratagene mouse heart (#937316) Mus musculus cDNA clone IMAGE:536084 5' similar to gb:M22810 Mouse androgen-regulated protein mRNA, complete cds (MOUSE);, mRNA sequence. | Mus musculus |
| 4 ☐ | AA073010 | mm94c11.r1 Stratagene mouse heart (#937316) Mus musculus cDNA clone IMAGE:536084 5', mRNA sequence. | Mus musculus |
| 5 ☐ | AA073011 | mm94c09.r1 Stratagene mouse heart (#937316) Mus musculus cDNA clone IMAGE:536086 5' similar to gb:X70847 | Mus musculus |

FIG. 7

Select the fields you want to view, select how you would like to sort the data and press

Show Collection

| | | | |
|---|---|---|---|
| ☐ Accession | ☐ IMAGE Identifier | ☐ Alias protein |
| ☐ Expression level data | ☐ Xhyb analysis | ☐ Phenotype |
| ☐ Unique Identifier | ☐ Tissues | ☐ Phenotype ID/ OMIM ID |
| ☐ Title | ☐ GDB | ☐ Chromosome |
| ☐ PubMed | ☐ Gene name | ☐ Map location |
| ☐ Related Proteins | ☐ Gene Function | ☐ Map link |
| ☐ Related Sequences | ☐ Synonyms | ☐ Map type |
| ☐ Taxonomy | ☐ Pathway | ☐ STS-marker name |
| ☐ Repeats | ☐ SNP analysis | ☐ STS-chromosome |
| ☐ Hairpin/Palindrome | ☐ Unigene ID | ☐ STS-ID |
| ☐ Homology | ☐ Locus ID | ☐ Reviewed RefSeq |
| ☐ Research Genetics Clone | ☐ Alias symbol | ☐ cDNA Source |

Sort Preferences

1. Unigene ID ▼
2. Locus ID ▼
3. Reviewed RefSeq ▼
4. Repeats ▼
5. Chromosome ▼

FIG. 10

Arrogant Server

Welcome to the ARROGANT (ARRay ORGANizing Tool) Server, please move back and forth between this page and the earlier page to choose the fields to be viewed and fields to be sorted on.

For more information on any input data field click on that link. For example, for help on Accession click on Accession

*Databases Updated When?*

| Database | Genbank | Pompous | Locuslink | Unigene | Research Genetics |
|---|---|---|---|---|---|
| Last Updated | 2/7/01 8:06:55 AM | 1/18/01 8:35:24 AM | 2/6/01 8:34:29 AM | 1/28/01 8:34:45 AM | 1/8/01 8:35:59 AM |

Download results table in excel format

*Results Table*

| Record | Accession | Uni ID | Cluster ID | Title | Homologs | Gene Type/Function |
|---|---|---|---|---|---|---|
| 1. ☐ | NM 000236 | 4557722 | Hs. 9994 | Homo sapiens lipase, hepatic (LIPC), mRNA. | Mm.362, Rn.1195 | Summary: LIPC encodes hepatic triglyceride lipase which is expressed in liver. LIPC has dual functions of triglyceride hydrolase and ligand bridging factor for receptor mediated lipoprotein uptake |
| 2. ☐ | NM 00023 | 4506910 | Hs. 99931 | Homo sapiens sarcoglycan, alpha (50kD dystrophin-associated glycoprotein) (SGCA), mRNA. | Mm.18709, Rn.23558 | |
| Summary Record | 239 Accession | 232 Uni ID | 207 Cluster ID | 232 Title | 201 Homologs | 239 Gene Type/Function |

FIG. 11

| Column Name | Datatype | Length | Precision | Scale | Allow Null | Default Value |
|---|---|---|---|---|---|---|
| accsno | varchar | 9 | 0 | 0 | ☐ | |
| nid | varchar | 10 | 0 | 0 | ☑ | ((-1)) |
| defn | varchar | 255 | 0 | 0 | ☑ | ((-1)) |
| type | varchar | 100 | 0 | 0 | ☑ | ((-1)) |
| dna | varchar | 6 | 0 | 0 | ☑ | ((-1)) |
| organism | varchar | 25 | 0 | 0 | ☑ | ((-1)) |
| source | varchar | 25 | 0 | 0 | ☑ | ((-1)) |
| keyword | varchar | 6 | 0 | 0 | ☑ | ((-1)) |
| comments | varchar | 255 | 0 | 0 | ☑ | ((-1)) |
| featstuff | varchar | 1400 | 0 | 0 | ☑ | ((-1)) |
| fstart | varchar | 10 | 0 | 0 | ☑ | ((-1)) |
| fend | varchar | 10 | 0 | 0 | ☑ | ((-1)) |
| species | varchar | 200 | 0 | 0 | ☑ | ((-1)) |
| authors | varchar | 255 | 0 | 0 | ☑ | ((-1)) |
| journal | varchar | 255 | 0 | 0 | ☑ | ((-1)) |
| version | varchar | 30 | 0 | 0 | ☑ | ((-1)) |
| reference | varchar | 25 | 0 | 0 | ☑ | ((-1)) |
| title | varchar | 100 | 0 | 0 | ☑ | ((-1)) |
| basepair | varchar | 10 | 0 | 0 | ☑ | ((-1)) |

FIG. 13

| unidata | |
|---|---|
| ☐ | cluster id |
| ☐ | accession |
| ☐ | type |

| uniotherprotein | | |
|---|---|---|
| ☐ | clusterid | ▲ |
| ☐ | otherproids | ▼ |

| uniprotein | |
|---|---|
| ☐ | clusterid |
| ☐ | pro org |
| ☐ | pro id |
| ☐ | similarity |

| unitissue | | |
|---|---|---|
| ☐ | UG | ▲ |
| ☐ | tissue | ▼ |

| unistuff | |
|---|---|
| ☐ | UG |
| ☐ | express |
| ☐ | locuslink |
| ☐ | title |
| ☐ | gene |
| ☐ | cytoband |
| ☐ | sts |
| ☐ | mql |
| ☐ | chromosome |

| pathway |
|---|
| UniqueId |
| pathno |
| organism |

| lookpath |
|---|
| pathno |
| pathway |

| Kegg |
|---|
| UniqueId |
| LocusId |
| Organism |
| Name |
| Defn |
| class |
| position |
| gdb |
| ncbi |

FIG. 17

| homoortho |
|---|
| Unigid1 |
| Unigid2 |
| Locid1 |
| Locid2 |
| Acc1 |
| Acc2 |

| RG_Hs_seq_ver_101100 |
|---|
| ☐ [Release Number] |
| ☐ [RG Plate] |
| ☐ [RG row] |
| ☐ [RG column] |
| ☐ [Insert Size*] |
| ☐ [Cluster ID] |
| ☐ [UG build] |
| ☐ [Clone ID] |
| ☐ Vector |
| ☐ Tissue |
| ☐ Library |
| ☐ Accession |
| ☐ NID |
| ☐ [Gene Name] |
| ☐ [Gene Symbol] |
| ☐ Chromosome |
| ☐ Band |
| ☐ Markers |
| ☐ Col019 |
| ☐ Barcode |
| ☐ Antibiotics |
| ☐ [repeat ?] |

FIG. 18

COMPUTER-BASED METHOD FOR CREATING COLLECTIONS OF SEQUENCES FROM A DATASET OF SEQUENCE IDENTIFIERS CORRESPONDING TO NATURAL COMPLEX BIOPOLYMER SEQUENCES AND LINKED TO CORRESPONDING ANNOTATIONS

The research carried out in the subject application was supported in part by grants from the National Institutes of Health (Grant No. 4-R33-CA81656-02). The government may have rights in this invention.

FIELD OF THE INVENTION

The field of the invention is computational design and analysis of arrays of genomic data and products.

BACKGROUND OF THE INVENTION

With the completion of the Human Genome Project, genetic research is now being directed towards understanding complex multigenic diseases e.g. cancer, cardiac diseases. Microarray technology has proven to be really useful in studying the expression pattern of thousands of genes simultaneously. Also with the availability of the entire genome, many tools have now been developed to generate inferences and predictions based on the entire genome, such as POMPOUS (Fondon et al, PNAS, 95(13)7514–9, 1998) which looks for potentially polymorphic genes. Efforts like Program For Genome Application (PGA) are now being undertaken to study hundreds of genes associated with particular diseases or phenotypes. As a result, researchers frequently need to compile large lists of genes associated with certain diseases, phenotypes, keywords and their synonyms. The selection of array elements for large gene collections typically involves: finding possible gene candidates, generally done using a series of keyword searches on different databases; assembling these several different lists obtained from various databases and trying to eliminate redundancies; and annotating all the genes (on the tentative list) in detail so that the researcher can know as much as possible about the gene.

The NCBI website provides a keyword search engine for various databases like GenBank, UniGene and LocusLink; however, the keyword search has to be done separately on each database. The list then needs to be combined and more importantly, the sequence redundancy needs to be eliminated. Eliminating the redundancy manually is not an easy task since each database has its own unique identifier. This is primarily done based on the researcher's experience and not all sequence redundancies are eliminated, especially for a large collection of genes. Additionally, the annotation for all the candidates on the list is not available in one place, so the researcher has to look up individual genes—a very laborious and time-consuming task.

Websites like Genecards (Rebhan, M et al, Bioinformatics 14(8)656–64, 1998) <http://nciarray.nci.nih.gov/cards/>) provide a database of human genes, their products and their involvement in diseases. However, Genecards only offers information about the functions of all human genes that have an approved symbol, and a few selected others. Again this information can only be accessed one gene at a time, and the annotation cannot be downloaded in any useful format for working with a large gene collection. DRAGON (Bouton CM et al, Bioinformatics 16(11)1038–9, 2000)<http://207.123.190,10/dragon.htm>) lets the researcher do a keyword search on multiple databases at one time, but the output is a list of accession numbers and definitions in text format, which is not linked to any of its annotations. The tool does not let the researcher select entries from the keyword search. It does not allow moving between pages and merge lists obtained from different keyword searches. As a result DRAGON does not help in systematically compiling a large gene collection. Further, DRAGON does not include important databases like GenBank and LocusLink that are the most commonly used databases for searching candidate genes. None of these tools helps in eliminating sequence redundancies within the lists. Databases like LocusLink and Genecards attempt to integrate the unique characteristics from various databases and provide a broad summary on a single gene basis. Nevertheless they do not help in annotating a large gene collection. There is a need for a tool tat comprehensively gathers annotation related to all these elements in one place. The annotation tool of DRAGON only combines information from UniGene, Swissprot, Pfam and KEGG pathway database with 17 fields of annotation. However these fields do not include important fields like repeat, SNP, pathways, clones, etc. which would be of great value. Additionally including a number (expression data for microarrays, purity of repeats for polymorphism) in the final annotation table would make it convenient for the user to extract infonnation from the table. With more and more gene collections, it is also required to combine several collections of genes, obtained from different sources.

The production of DNA microarrays can be divided into four stages: a. Selection of array elements and design of the probe DNA; b. Preparation of the probe DNA; c. Preparation of a suitable design substrate to spot the probes on; d. Deposition of array elements. The selection of array elements for microarays involves assembling a large gene collection. It would be very valuable if the same tool (to compile a large gene collection) could be used to further design primers, look for commercially available clones (expression microarrays) and design resequencing probes (resequencing microarrays). Once the genes are spotted on the microarray and hybridized to fluorescent labeled probes, there are a number of software programs that help in conversion of the fluorescence of the scanned image to numbers, using complex mathematical corrections to extract signal from background noise. e.g. Genepix (<http://www.axon.com/GN GenePixSoftware.html>) and ArrayVision (<http://imaging.brocku.ca/products/Arrayvision.htm>). These numbers indicate level of expression. Other programs such as GeneSpring (Silva et al, HMS Beagle: The BioMed-Net Magazine issue 82, 2000), Cluster Treeview (Eisen MB et al, Proc Natl Acad Sci U S A 95) and Spotfire (<http://www.spotfire.com>), help in the analysis by clustering the data together using various methods based on K-means, hierarchal or self-organizing maps. Clustering algorithms use the expression level data to group the various elements on the array. It would also be very useful to view the elements of the array with their complete annotation and overlay the expression level data on top of it. The data could further be selectively viewed by sorting on various annotation fields and the expression level data. This approach could be useful to view any large gene collection in general. With the increasing number of microarray experiments, it would be valuable to compare elements between different microarrays considering that fragments of the same gene might be represented by different sequence identifiers. For example, two different accession numbers might belong to the same UniGene cluster, representing the same gene. An artifact sometimes observed in the results obtained from an expression profiling microarray experiment is that some sequences might hybridize to other sequences to which they are significantly similar. This leads to false positive results after a microarray experiment. Although Human Cot DNA is often used to prevent non-specific hybridization by blocking simple repetitive elements in genomic DNA, as shown in experiments to study cross-hybridization, Human Cot DNA is not very effective in preventing cross hybridization. ARROGANT computationally estimates the amount of cross hybridization for each sequence and tags potential genes as possible candidates for cross hybridization.

Several computational tools and databases are available which may be used in the development of the code for working with large gene collections. Some of them are discussed here in brief.

1. PRIMO: PRIMO (Li et al, Genomics 40(3) 476–85, 1997) is a code that was developed to design primers for large-scale DNA sequencing projects. PRIMO designs primers (short sequences typically 20 bases long), which are used to amplify sequences (0.4 KB–2 KB) using PCR. PRIMO can be made to design primers to amplify a specific region. PRIMO can be run in batch mode and the region for the design of primers for each sequence can be specified separately. The parameters file (including parameters like oligo length, melting temperatures etc.) can be altered. The code is written in ANSI C and is available locally on a HP/UX computer. The code has been successfully used to design primers for the past couple of years and is available on the web at <http://atlas.swmed.edu>. This makes PRIMO a very important tool to design primers to amplify a large number of sequences simultaneously.

2. BLAST: BLAST(Basic Local Alignment Search Tool) is an alignment tool to search for similar sequences (protein or DNA) developed by NCBI (Altschul et at, Journal of Molecular Biology 215(3)4-3-10,1990). It is available at <http://www.ncbi.nlm.nih.gov/BLAST/>. ARROGANT uses the BLAST output to estimate cross-hybridization for microarrays. Each element on the array is BLASTed against the entire UniGene database and the BLAST output is parsed to detect 65 contiguous hydrogen bond overlaps, used as a threshold for cross-hybridization.

3. Rep-X: Rep-X (Wren et al, American Journal of Human Genetics 67(2)345–56, 2000) uses the UniGene database and generates a list of repeats, hairpin and palindrome sequences. This code runs on HP/UX computer. The output of Rep-X is incorporated into ARROGANT to look for repeats, hairpins and palindrome sequences.

4. NCBI Databases: NCBI provides databases used by ARROGANT (downloaded and implemented locally) to annotate gene collections and find potential candidates associated with keywords. The databases include: a. GenBank (Benson D A et al, Nucleic Acids Res 28(1)15–18, 2000): An annotated collection of all publicly available DNA sequences provided by NIH; b. UniGene (Schuler, J Mol Med 75(10)694–8, 1997): Partitions GenBank EST sequences into a non-redundant set of gene oriented clusters; c. LocusLink (Pruitt et al, Nucleic Acids Res 29(1)137–40, 2001): Integrates and provides a single query interface to cluster sequences and makes available descriptive information about genetic loci; d.

HomoloGene (Zhang et al, J. Comp. Biol. 7(1–2)203–14, 2000): The database of calculated orthologs and homologs between all UniGene clusters by each pair of organisms.

5. KEGG Databases: KEGG (Kyoto Encyclopedia of Genes and Genomes) (Kanehisa, M., Oxford University Press 2000) provides genome and pathway databases for a large number of organisms. ARROGANT uses (downloaded and implemented locally) these databases to look for potential gene candidates, their pathways and to annotate gene collections.

6. Clone Databases: Commercially available clone databases include the IMAGE (G. Lennon et al, Genomics 33(1)151–2, 1996) Consortium, which shares high quality arrayed cDNA libraries and provides sequence, map, and expression data on the clones in these arrays to the public domain; vendors include Research Genetics, Incyte Genomics, etc.

SUMMARY OF THE INVENTION

The invention relates to computer-based systems and corresponding methods for the design and analysis of biopolymer sequence arrays.

In a first principal embodiment, the invention provides a computer-based system for creating a targeted collection of sequences from a dataset comprising sequence identifiers corresponding to natural complex biopolymer sequences and linked to corresponding annotations, the system comprising:

a) a search function which searches the annotations of the dataset according to a user-defined criterion and outputs a first subset of the dataset restricted by the criterion;

b) a redundancy reducing function which compares the first subset with a first database correlating the sequence identifiers of the first subset with syngeneic biopolymers and outputs a second subset of the dataset having reduced unique, natural complex biopolymer redundancy relative to the first subset;

c) a selection function which applies to the second subset a user-defined selection parameter and outputs a third subset restricted relative to the second subset by the parameter; and d) a tabulation function which creates and outputs the targeted collection of sequences in the form of a data table comprising, configurable by and sortable by the sequence identifiers of the third subset.

The system may optionally incorporate one or more of the following limitations:

the criterion is selected from the group consisting of a keyword and a concept;

the criterion is one of a plurality of user-defined criteria, and the search function searches the annotations of the dataset according to the criteria and outputs a first subset of the dataset restricted by the criteria;

the criterion is one of a plurality of user-defined criteria, and the search function searches the annotations of the dataset according to the criteria and outputs a first subset of the dataset restricted by the criteria, wherein the criteria include multiple keywords;

the dataset is selected from the group consisting of GenBank, Medline and KEGG;

the dataset is one of a plurality of datasets, and the search function searches the annotations of the datasets according to the user-defined criterion and outputs a first subset of the datasets restricted by the criterion;

the database is selected from the group consisting of UniGene and LocusLink;

the database is one of a plurality of databases correlating the sequence identifiers of the first subset with syngeneic biopolymers, and the redundancy reducing function compares the first subset with the databases and outputs the second subset of the dataset;

the parameter is selected from the group consisting of source, species, author and pathway;

the parameter is one of a plurality of user-defined selection parameters, and the selection function applies to the second subset the parameters and outputs the third subset restricted relative to the second subset by the parameters;

the redundancy reducing function outputs a second subset of the dataset which eliminates unique, natural complex biopolymer redundancy relative to the first subset; and the system further comprises an expansion function which searches a second database for synonyms of the sequence identifiers of the first, second or third subset.

In a second principal embodiment, the invention provides a computer-based system for creating a targeted collection of sequences from a plurality of datasets comprising sequence identifiers corresponding to natural complex biopolymer sequences, the system comprising:

a) a merge and redundancy reducing function which compares the datasets with a database correlating the sequence identifiers with syngeneic biopolymers and creates a subset of the sum of the datasets having reduced unique, natural complex biopolymer redundancy relative to the sum; and b) a tabulation function which creates and outputs the targeted collection of sequences in the form of a data table comprising, configurable by and sortable by the sequence identifiers of the subset.

The system may optionally incorporate one or more of the following limitations:

the merge and redundancy reducing function further comprises a selection function which applies a user-defined selection parameter whereby the subset is restricted relative to the sum of the datasets by the parameter; and the merge and redundancy reducing function further comprises a selection function which applies a user-defined selection parameter whereby the subset is restricted relative to the sum of the datasets by the parameter, wherein the parameter is selected from the group consisting of source, author and pathway.

In a third principal embodiment, the invention provides a computer-based system for creating a targeted collection of sequences from a dataset comprising sequence identifiers corresponding to natural complex biopolymer sequences and linked to corresponding first annotations, the system comprising:

a) an integration function which merges the dataset with a database comprising second annotations attributable to and correlated with at least a subset of the sequence identifiers or sequences of the dataset and which links the second annotations to the corresponding sequence identifiers of the subset; and b) a tabulation function which creates and outputs the targeted collection of sequences in the form of a data table comprising, configurable by and sortable by the sequence identifiers of the subset and the second annotations.

The system may optionally incorporate the following limitation:

the second annotations comprise data attributable to and correlated with at least a subset of the sequence identifiers or sequences of the dataset, said data selected from the group consisting of: gene expression data, sequencing data, genotype data, polymorphism data and clinical data.

In yet another embodiment, the invention provides a computer-based system incorporating the elements of the first, second, and optionally, the third principal embodiments described herein.

In a particular embodiment, the recited systems and methods have been implemented in a computer tool called ARROGANT. This program has been developed to facilitate the identification, analysis and comparison of collections of genes or clones. ARROGANT, in the analysis mode, is a comprehensive tool for providing annotation to large gene collections. ARROGANT takes in a large collection of gene identifiers and associates it with other information collected from many sources like sequence annotations, pathways, homology, polymorphisms, artifacts etc. to help the researcher draw scientific conclusions, understanding, and proceed with future experiments. The simultaneous annotation for a large assembly of genes makes the collection of genomic/EST sequences truly informative. For example, if the collection of genes is used for microarrays, ARROGANT predicts cross-hybridization with the members on the array and the entire UniGene database to help the researcher to design probes that avoid cross-hybridization or alerts the user of their presence. In the design mode, ARROGANT assists in compiling a gene collection, using several different databases simultaneously, queried with keywords and their synonyms. ARROGANT, in one integrated package, also facilitates the design of expression/resequencing microarrays by designing primers, looking for commercially available clones and designing probes for resequencing. The package also has a third mode of operation to eliminate sequence redundancies and duplicates from multiple gene collections. This is very useful in identifying redundancies due to sequences or clones having different accession numbers but representing fragments of the same gene. This simplifies comparing experiments from various research groups. ARROGANT has been successfully applied to many large gene collections for microarrays, complex multigenic trait projects, polymorphism discovery projects etc.

BRIEF DESCRIPTION OF THE FIGURES

FIG. 6: Input page of ARROGANT in design mode.

FIG. 7: Sample output of ARROGANT from keyword search.

FIG. 10: Selection of fields and selection of sort parameters page.

FIG. 11: Final display page for analysis mode.

FIG. 13: Schema for GenBank database

FIG. 14: Schema for UniGene database

FIG. 15: Schema for LocusLink database

FIG. 16: Schema for KEGG database

FIG. 17: Schema for HomoloGene database

FIG. 18: Schema for Research Genetics clone database

DETAILED DESCRIPTION OF PARTICULAR EMBODIMENTS OF THE INVENTION

Figure 1:
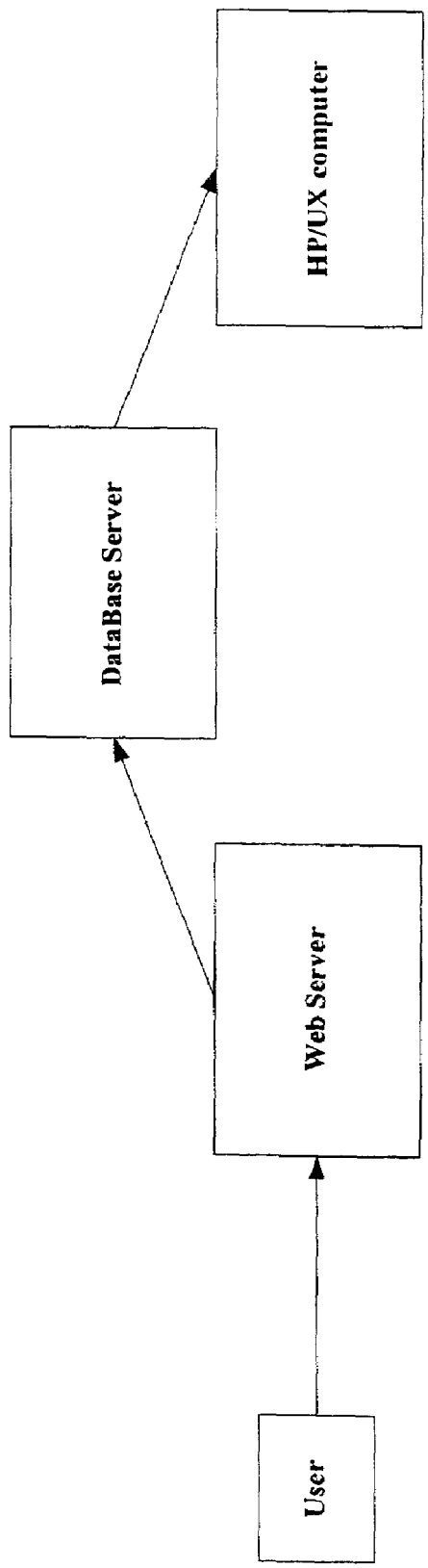
FIG. 1: Distribution of ARROGANT over three separate servers.

The following descriptions of particular embodiments and examples are offered by way of illustration and not by way of limitation.

The invention relates to computer-based systems and corresponding methods for the design and analysis of complex biopolymer sequence arrays. The recited biopolymer sequences are polypeptide or polynucleotide sequences, preferably natural sequences, and the arrays may be conceptual, digital arrays or tangible, molecular arrays (i.e. solid phase biochips). While exemplified with a server and web based application, the functionalities of the systems may be implemented in any convenient algorithm on any convenient platform, stored in any convenient medium, and accessed through any convenient port and interface. The functionalities of the recited systems may be independently segregated or two or more functionalities may be implemented together in a single process. Similarly, in the corresponding methods, the steps may be independently segregated or two or more steps may be effected contemporaneously. Of course, the recited systems and methods may further comprises further functionalities and steps to accomodate user preferences and database requirements and these may be implemented in concert or independently of those recited.

In a first principal embodiment, a design mode operation, the invention provides a computer-based system for creating a targeted collection of sequences from a dataset comprising sequence identifiers corresponding to natural complex biopolymer sequences and linked to corresponding annotations. For example, in the design mode, the system can compile a collection of genes and/or proteins relevant to a user-determined study. The system is amenable to any selected nomenclature of sequence identifiers, such as accession numbers and a wide variety of corresponding annotations, which may include such attributes as source species, author, deposit date, associated diseases and pathways, polymorphisms, length, etc. Similarly, the system is amenable to any convenient dataset, unconstrained by size, complexity or public availability. Exemplary datasets include locally maintained datasets, GenBank, Medline, KEGG, etc. Furthermore, the system can implement a plurality of datasets, preferably at least three, more preferably at least five, simultaneously or sequentially.

In this first embodiment, the system effects four functionalities. The first functionality is a search function which searches the annotations of the dataset according to a user-defined criterion and outputs a first subset of the dataset restricted by the criterion. The user may select any criterion encompassed by annotations of the dataset(s), including keyword and more concept-based search criteria. Furthermore, the criterion is preferably one of a plurality of user-defined criteria, preferably at least three, more preferably at least five, and may include multiple keywords, such as "cardiac disease", and preferably uses logical operators like 'and/or", and the search function searches the annotations of the dataset according to all the criteria and outputs a first subset of the dataset restricted by the criteria.

The second functionality is a redundancy reducing function which compares the first subset with a first database correlating the sequence identifiers of the first subset with syngeneic biopolymers and outputs a second subset of the dataset having reduced unique, natural complex biopolymer redundancy relative to the first subset, and preferably, which substantially eliminates unique, natural complex biopolymer redundancy relative to the first subset (i.e. wherein the second subset of the dataset has no unique, natural complex biopolymer redundancy). The database need not be perfectly syngeneically ordered (i.e. natural polynucleotides or polypeptides ordered by common source gene) and the recited correlation need not be perfect, but only sufficient to effect the required reduction in redundancy. Exemplary databases include locally maintained syngeneically ordered databases, UniGene and LocusLink. Preferably, the database is one of a plurality of databases, preferably at least three, more preferably at least five, correlating the sequence identifiers of the first subset with syngeneic biopolymers, and the redundancy reducing function compares the first subset with the databases and outputs the second subset of the dataset.

The third functionality is a selection function which applies to the second subset a user-defined selection parameter and outputs a third subset restricted relative to the second subset by the parameter. As with the recited criterion, the used may select any parameter encompassed by annotations of the dataset(s), including source, species, author and pathway parameters. Furthermore, the paramter is preferably one of a plurality of user-defined selection parameters, preferably at least three, more preferably at least five, and preferably uses logical operators like 'and/or", and the selection function applies to the second subset the parameters and outputs the third subset restricted relative to the second subset by the parameters.

The fourth functionality is a tabulation function which creates and outputs the targeted collection of sequences in the form of a data table comprising, configurable by and sortable by the sequence identifiers of the third subset. The data table generally includes a variety of information related to each sequence identifier. The data table may be exported in any convenient format, preferably a format that is platform-independent, web-browser compatible and/or widely used, e.g. text, tab delineated, commercial database format, e.g. Excel, Access, etc., etc.

This first principal embodiment preferably also comprises an expansion function which searches a second database for synonyms of the sequence identifiers of the first, second or third subset; note that the first database may be the same as the dataset.

In a second principal embodiment, a comparison mode operation, the invention provides a computer-based system for creating a targeted collection of sequences from a plurality of datasets comprising sequence identifiers corresponding to natural complex biopolymer sequences, the system comprising two functionalities. For example, in the comparison mode, the system can resolve overlapping collection members, even if they have different identifiers for the same object. The system is amendable to comparing any of a wide variety of empirically, conceptually or computationally-derived databases and may operate to groupwise (e.g. pairwise) or simultaneously compare at least two, preferably at least three, more preferably at least five different datasets.

The first functionality of this comparison mode of operation is a merge and redundancy reducing function which compares the datasets with a database correlating the sequence identifiers with syngeneic biopolymers and creates a subset of the sum of the datasets having reduced, and preferably substantially eliminated unique, natural complex biopolymer redundancy relative to the sum. As with the design mode, the database need not be perfectly syngeneically ordered (i.e. natural polynucleotides or polypeptides ordered by common source gene) and the recited correlation need not be perfect, but only sufficient to effect the required reduction in redundancy. Similarly, the merge and redundancy reducing function may further comprise a selection function which, analogously with the design mode, applies a user-defined selection parameter whereby the subset is restricted relative to the sum of the datasets by the parameter.

The second functionality of the comparison mode is a tabulation function which creates and outputs the targeted collection of sequences in the form of a data table comprising, configurable by and sortable by the sequence identifiers of the subset. As with the design mode, the data table may be exported in any convenient format, preferably a format that is platform-independent, web-browser compatible and/or widely used, e.g. Excel, Access, etc.

In a third principal embodiment, an analysis mode operation, the invention provides a computer-based system for creating a targeted collection of sequences from a dataset comprising sequence identifiers corresponding to natural complex biopolymer sequences and linked to corresponding first annotations. As with the design mode, this system is amenable to any selected nomenclature of sequence identifiers, such as accession numbers and a wide variety of corresponding annotations, which may include such attributes as source species, author, deposit date, associated diseases and pathways, polymorphisms, length, etc. Similarly, the system is amenable to any convenient dataset, unconstrained by size, complexity or public availability. Furthermore, the system can implement a plurality of datasets, preferably at least three, more preferably at least five, simultaneously or sequentially.

The first functionality of the analysis mode of operation is an integration function which merges the dataset with a database comprising second annotations attributable to and correlated with at least a subset of the sequence identifiers or sequences of the dataset and which links the second annotations to the corresponding sequence identifiers of the subset. The second annotations may be any of a wide variety of empirically, conceptually or computationally-derived annotations, such as data attributable to and correlated with at least a subset of the sequence identifiers or sequences of the dataset. Any measurable data may be used, including gene expression data, sequencing data, genotype data, polymorphism data and clinical data.

The second functionality of the analysis mode of operation is a tabulation function which creates and outputs the targeted collection of sequences in the form of a data table comprising, configurable by and sortable by the sequence identifiers of the subset and the second annotations. As with the design and merge modes, the data table may be exported in any convenient format, preferably a format that is platform-independent, web-browser compatible and/or widely used, e.g. text, tab delineated, commercial database format such as Excel, Access, etc., etc.

In yet another embodiment, the invention provides a computer-based system incorporating the elements of the first, second, and optionally, the third principal embodiments described herein. In an alternative embodiment, the invention provides a system for the design and analysis of complex biopolymer sequence matrices, said system comprising:

(a) a sequence input function which accepts user-defined sequences;

(b) a sequence criteria input function which accepts user-defined instructions for sequence search criteria according to function or structure;

(c) a sequence search function which operates on said criteria to search biopolymer sequence databases according to said criteria to identify a population of diverse yet functionally or structurally restricted sequences;

(d) a sequence population processing function which expands said population to encompass synonymous sequences and condenses said population by combining into common elements sequences which are syngeneic;

(e) a matrix output function which presents results of said processing as a matrix of elements corresponding to unique, syngeneic sequences;

(f) a matrix data input function which accepts user-determined matrix sequence data;

(g) matrix sort, search and filter input functions which accept user-defined instructions for sorting, searching and filtering matrix sequences;

(h) a sequence matrix sort function which operates on said sorting instructions to sort matrix sequences;

(i) a sequence matrix search function which operates on said searching instructions to search matrix sequences;

(j) a sequence matrix filter function which operates on said filtering instructions to filter matrix sequences;

(k) a report generating function which provides reports of the filtered matrix sequences; and (l) a graphical user interface which provides fields for user inputting of the user-defined sequences, the search and processing criteria, the user-defined instructions for the sort, search and filter input functions, and for user visualization of the reports.

EXAMPLE

This design, comparison and analysis modes described above have been implemented in the computer tool known as ARROGANT. ARROGANT, in one integrated package, assists in compiling a gene collection starting from keywords and their synonyms, designs primers, looks for commercially available clones and designs probes for resequencing. Its focus is to enable the researcher to simultaneously work with a large collection of genes, their information and experimental data. Once a gene collection has been refined by the researcher (the design mode), ARROGANT then annotates the collection from many databases (the annotation mode). Experimental data can then be analyzed by association with this information (sequence annotations, pathways, homology, artifacts etc.) to aid in drawing scientific conclusions. In a large gene collection, sequence redundancies and naming differences can be resolved by ARROGANT (the collection comparison mode). ARROGANT calls upon the resources of several computers and many databases to design, annotate and compare collections. Once this computation is done, the collection can be manipulated, and experimental data can be integrated with it on a PC-based database server via a web server.

(a) Features/Capabilities

Finds possible gene collection candidates by doing a keyword search on multiple databases.

Provides a comprehensive annotation for large list of genes.

The annotation is presented as a table, which can be downloaded and used for later reference; thus there is no need to follow any links to gather annotation.

The annotation table is searchable and sortable.

Experimental microarray, sequencing or other data can be overlayed on the annotation table.

Eliminates sequence redundancies and duplicates by eliminating sequences having different accession numbers but representing fragments of the same gene.

Combines several different lists of genes and provides the set of unique genes.

Designs primers for a large list of genes and lets the user design primers either in the 3' end or in the random region.

Looks for commercially available clones.

Designs oligonucleotide probe sequences for resequencing microarrays.

Estimates the amount of cross-hybridization expected for each probe.

(b) Hardware Requirements

Compute Server: Hardware-independent; run under HP/UX 11.00.

Database Server: Requires Windows NT/2000 and SQL Server 7.0.

Web Server: Win NT/2000 and IIS.

(c) Software Requirements

Internet information web server

ASP

SQL Server 7.0

Visual basic 6.0 perl 5.005 or higher

BLAST (works with both WU-BLAST and NCBI-BLAST)—a code that identifies DNA or protein sequence similarity.

PRIMO (UTSW)—a code that designs DNA primers for laboratory experiments.

NCBI Tools (to get a fasta file for any accession number and to make a file BLASTable)

(d) Databases Implemented

GenBank: DNA sequence database.

UniGene: database of clusters of DNA sequence that approximate those of genes.

LocusLink: database that links individual genes, their synonyms and all individual DNA sequence files that are associated with them.

KEGG Genome and Pathways: database of connections between networks of genes.

Research Genetics Clone Database: database of the commercially available clones.

Repetitive Element Database (Rep-X): database of potential polymorphic repeat sites that can be causative for disease.

HomoloGene: database of genes that have homologies in other species.

Section 1: Introduction to ARROGANT

ARROGANT is a database driven tool developed to compile, annotate and merge large gene collections. NCBI, KEGG, Research Genetics and other custom databases have been implemented locally since they were the most commonly used databases and were found to extensively cover various items of information related to sequences. The local implementation of various databases and tools (e.g. PRIMO, BLAST) makes ARROGANT independent of other applications and significantly improves its performance. The modular design facilitates addition of new databases with relative ease. ARROGANT has three modes of operation: 1. Design mode (<http://arrogant.swmed.edu/index1.asp>) 2. Analysis mode (<http://arrogant.swmed.edu/index2.asp>) 3. Merge gene collections mode (<http://arrogant.swmed.edu/index3.asp>). The design mode includes keyword searching for compiling gene collections and helps in the design of expression and/or resequencing microarrays. ARROGANT facilitates the design of resequencing and/or expression microarrays by looking for commercially available clones, designing primers and designing probes for resequencing. The analysis mode annotates large gene collections and estimates cross-hybridization for microaaays. When used for microarrays, ARROGANT takes over where ratios or clustering of sequences finishes to provide important data about genes and enables researchers to get a global view. ARROGANT has been used to pre-compute annotation for a large number of gene collections (<http://arrogant.swmed.edu/precomute.asp>), and the results are stored in the database. This allows quick retrieval of the data and lets the researcher dynamically sort the annotation table. The merging gene collection mode is used to avoid duplicates and redundancies in collections. ARROGANT provides a web based interface and hyperlinks various fields displayed in all the three modes.

Section 2: ARROGANT Features

1. Compiles large gene collections starting from keywords: In a typical keyword search the researcher has to go to several different websites to look for genes of interest. After getting separate lists from different websites, she must combine them and avoid duplicates. ARROGANT facilitates this process by implementing several databases locally and providing simultaneous access to all of them. The databases may include major publicly available databases like GenBank, Unigene, polymorphism databases, clone databases, etc., and the keyword search may be done using Boolean operators like 'AND'/'OR'.

2. Annotates large gene collections: One of the main features of the analysis mode is to gather all the relevant information from different databases for a large collection of genes and present it as a searchable and sortable table rather than merely providing links to them. This table may be downloaded as a Microsoft Excel spreadsheet. The user is able to sort the data on different fields to enable her to select only a part of data to be viewed having certain characteristics, permitting biologically significant observations. For example, the data may be sorted based on repeats followed by map location to find some correlation between the ones having repeats on the array and their position in the genome.

3. Designs primers for a large set of genes: Once a large collection of genes is compiled it is useful to design primers (to amplify sequences using PCR) for them simultaneously. The parameters for design of the primers may be set by the user, which may include melting temperature, oligo length and number of primers in each direction. Additionally there is an option to automatically design primers in 3' end or random exon region.

4. Finds commercially available clones: Typically spotted microarrays consists of either cDNA clones and/or PCR products. It is generally cheaper to buy the clones for a large collection of genes than to amplify them by PCR. ARROGANT is able to search for commercially available clones and the search for clones may be based upon UniGene cluster identifiers to avoid redundancies.

5. Designs probes for resequencing: Resequencing microarrays consist of short sequences of 20–25 bases called probes. ARROGANT is able to output resequencing probes to be directly used by the Digital Optical Chemistry (DOC) project to make oligonucleotide microarrays.

6. Tags cross-hybridization artifacts for expression microarray: Cross-hybridization is caused due to sequences sharing regions of high sequence identity that leads to false positives on the array. Another feature of the tool is to computationally estimate the amount of cross hybridization for each member on the array.

7. Integrates experimental data: The tool is able to input an additional decimal number to be associated with each sequence. The number may correspond to expression data for microarrays, purity of repeats for polymorphism studies, priority level for a gene in a collection, etc.

8. Provides Web based interface: The program is available for the users to be accessed over the web without the need to install any additional software. The web based user-friendly interface isolates the researcher from the complexities of the code and makes it a more widely used tool.

9. Adds hyperlinks: The data presented by the tool may be hyperlinked to its source. For example, accession numbers may be hyperlinked to their GenBank annotation. Although basic ARROGANT provides extensive coverage to various items of information, adding hyperlinks enables the researcher to view thier original source.

Section 3: Materials and Methods 3.1 Computational Tools: For optimal performance of ARROGANT, we distributed the project into three different components: ARROGANT required implementation of many different databases locally; the web-based interface communicates with the databases to store and retrieve data; ARROGANT implements other codes including PRIMO (to design primers), BLAST (to estimate cross hybridization) and FormatDB (to retrieve sequences for given GenBank identifiers). These three components (Database, Web-Interface and programs on HP/UX computer) were implemented on three dedicated computers for optimal performance as shown in FIG. 1. The 'Database Server' has different databases implemented locally in a relational database format. 2. The 'Web Server' is used to host web pages for input and output of ARROGANT. 3. The programs running on HP/UX computer were utilized by developing an application in Microsoft Visual Basic 6.0 to communicate, run code (using telnet) and transfer files between the database server and the HP/UX computers. SQL Server 7.0 was chosen as the database software because of its ability to handle very large databases (having more than a million entries). Oracle was the only other database program capable of handling such large databases efficiently but is relatively expensive as compared to SQL Server 7.0. A web scripting application, Active Server Page (ASP) was used to develop various input and display pages. Perl programming language, especially useful for string operations, was used to develop other supporting scripts like parsing through BLAST output files to count hydrogen bond overlaps. The hardware and software configuration details are further detailed below.

Figure 2:
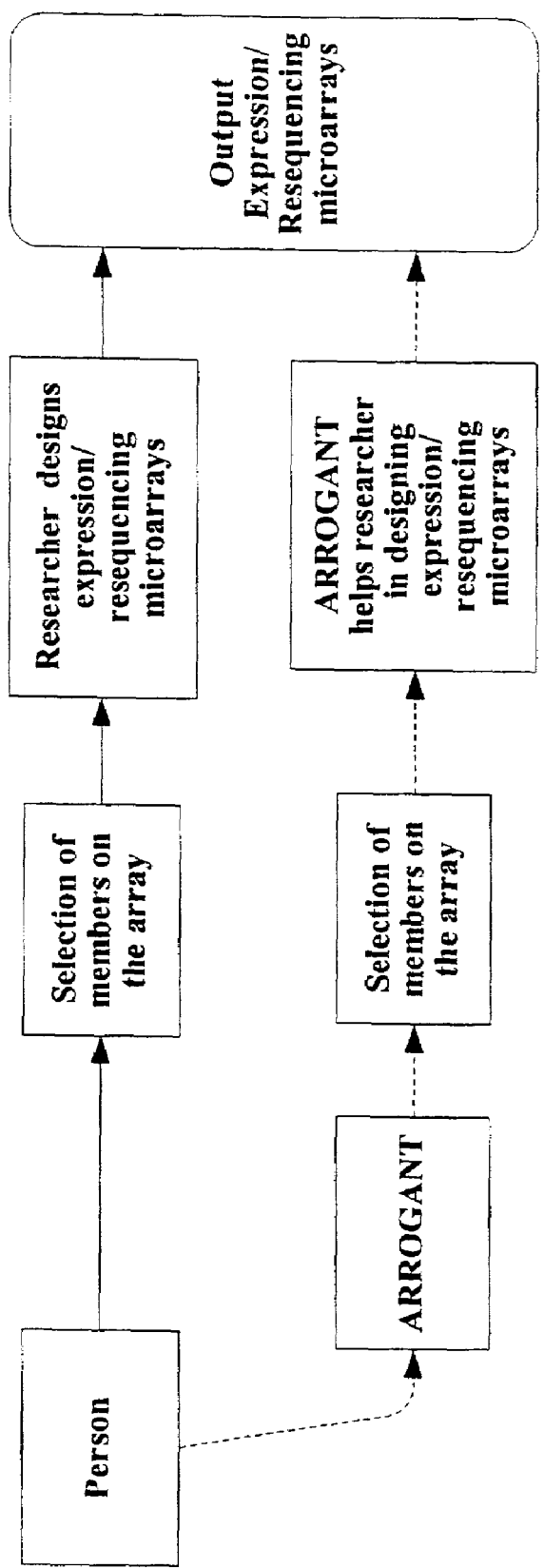
FIG. 2: Role of ARROGANT in designing expression/resequencing microarrays.
Figure 3:
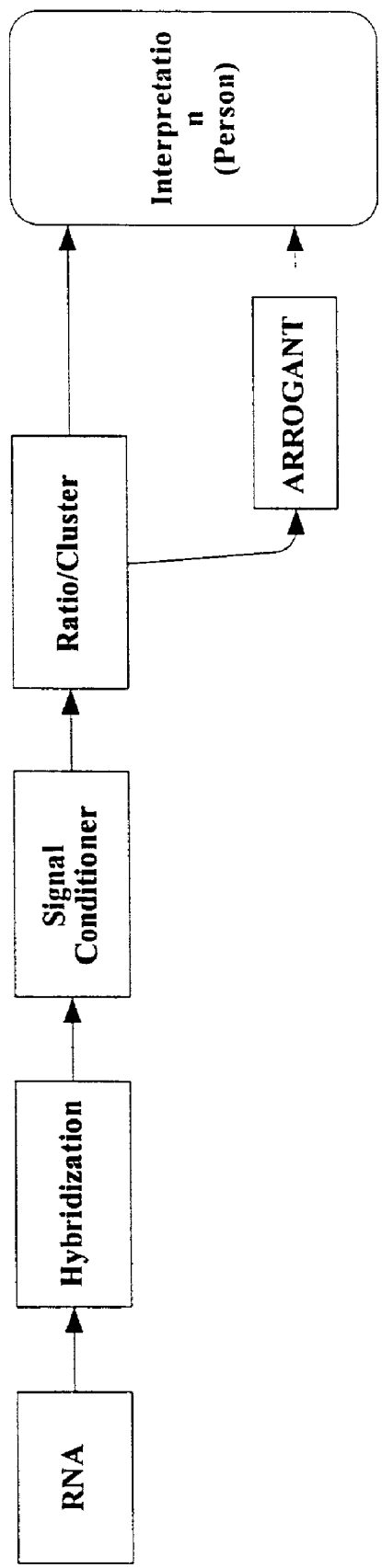
FIG. 3: Role of ARROGANT in analyzing microarray results.

3.2 Materials and Methods for microarray experiment: For the utilization of ARROGANT in a microarray experiment, the steps involved are outlined in FIGS. 2 and 3. The first step in the design of a microarray experiment is to select members to be included on the array. The researcher can search various databases like GenBank, dBEST, UniGene, etc. separately and combine into one list. ARROGANT helps in this process by enabling searching of candidate genes on several databases simultaneously. Once the members of the array are finalized, the next step is to look for the available clones or design primers for PCR. The output of a microarray experiment, genes correlated with expression level data, is usually fed into a clustering program. The researcher, based on her experience, has to interpret the results by individually going through different genes which are highly overexpressed or underexpressed. ARROGANT helps the researcher interpret the results by annotating all the genes in a tabular format and sorting the genes based on various items of information including expression level data.

3.3 Materials and methods PGA (Program for Genomic Application): PGA is a nationwide attempt to elucidate the basic mechanisms and cellular responses underlying injury and inflammation and to identify functionally significant polymorphisms in human genes. ARROGANT may be used to annotate all the genes in the PGA list to point out all the polymorphic repeats and at the same time provide various important information (e.g. pathways, map location, etc.) about each gene in the list. ARROGANT incorporates additional candidate genes assembled from literature, collective local expertise of participating investigators and from other PGA centers. ARROGANT will also be used in the design mode to look for new candidate genes compiled by participating investigators. The new candidate genes suggested will again be annotated as one table in the analysis mode of ARROGANT. Another application identifies informative DNA sequence polymorphisms with respect to inflammation and remodeling processes within the heart and vasculature by using genetic association studies in large population groups, supplemented by family studies.

Figure 4:
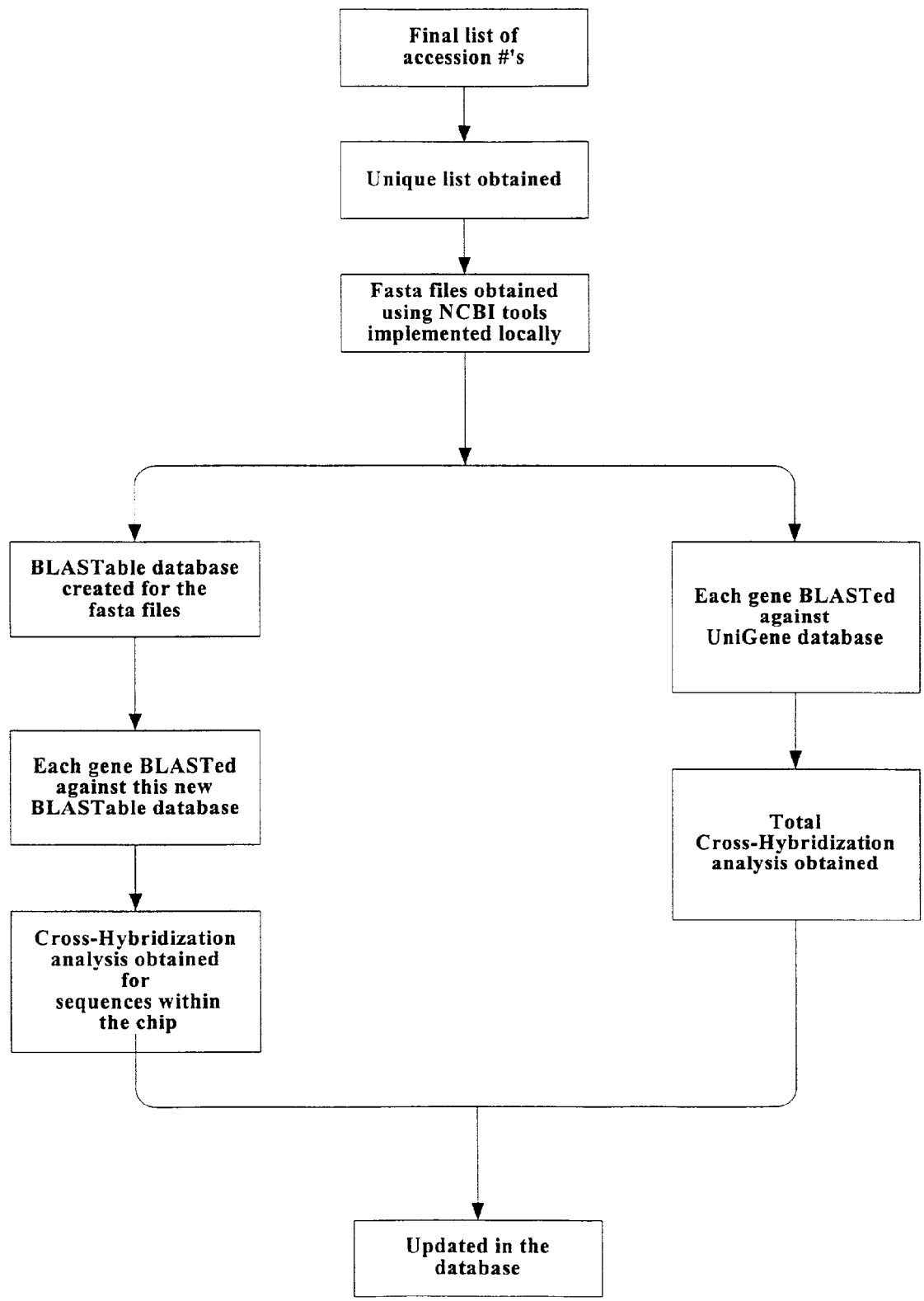
FIG. 4: Flowchart for method for estimation of cross-hybridization.

3.4 Materials and methods for cross-hybridization analysis: Yeast microarrays were used to study and quantify the effects of cross hybridization, as the entire yeast genome was available on a microarray. Each ORF (open reading frame) was BLASTed against every other ORF. The BLAST results were analyzed and the ORF's were ranked based on their sequence similarity to other ORF's. YBR112C was chosen as the target to be hybridized as it had the maximum sequence similarity to other ORF's. The results obtained from micro-array experiments were then analyzed to find co-relation between the amount of cross hybridization and the BLAST output to determine the threshold for cross hybridization computationally. Various numerical scores were used to correlate the BLAST output with the expression level data obtained from the experiments. These were: 1. BLAST core, 2. Contiguous basepair overlap, and 3. Contiguous hydrogen bond overlap. We observed that cross hybridization becomes significant if the number of contiguous hydrogen bond overlaps was more than 65. This was used by ARROGANT as a threshold to identify potential cross hybridization. The algorithm used by ARROGANT for identifying cross hybridization is illustrated in FIG. 4. Arrogant calculates cross hybridization in the analysis mode. A FASTA file for each gene on the array is obtained. Each sequence is BLASTed against every other sequence on the microarray and separately with the entire UniGene database. The results are tabulated as shown in Table 3.4.2 (two such tables are generated, one for potential cross hybridization by genes within the microarray and the other with the entire genome).

TABLE 3.4.2

Output table for the cross-hybridization analysis in the analysis mode.

| Gene | Number of potentially cross-hybridizing genes | Potentially cross-hybridizing genes | Maximum overlap | Sequence causing maximum overlap |
|---|---|---|---|---|
| <identifier> | <#> | <identitiers> | <#bp> | <sequence> |

Figure 5:
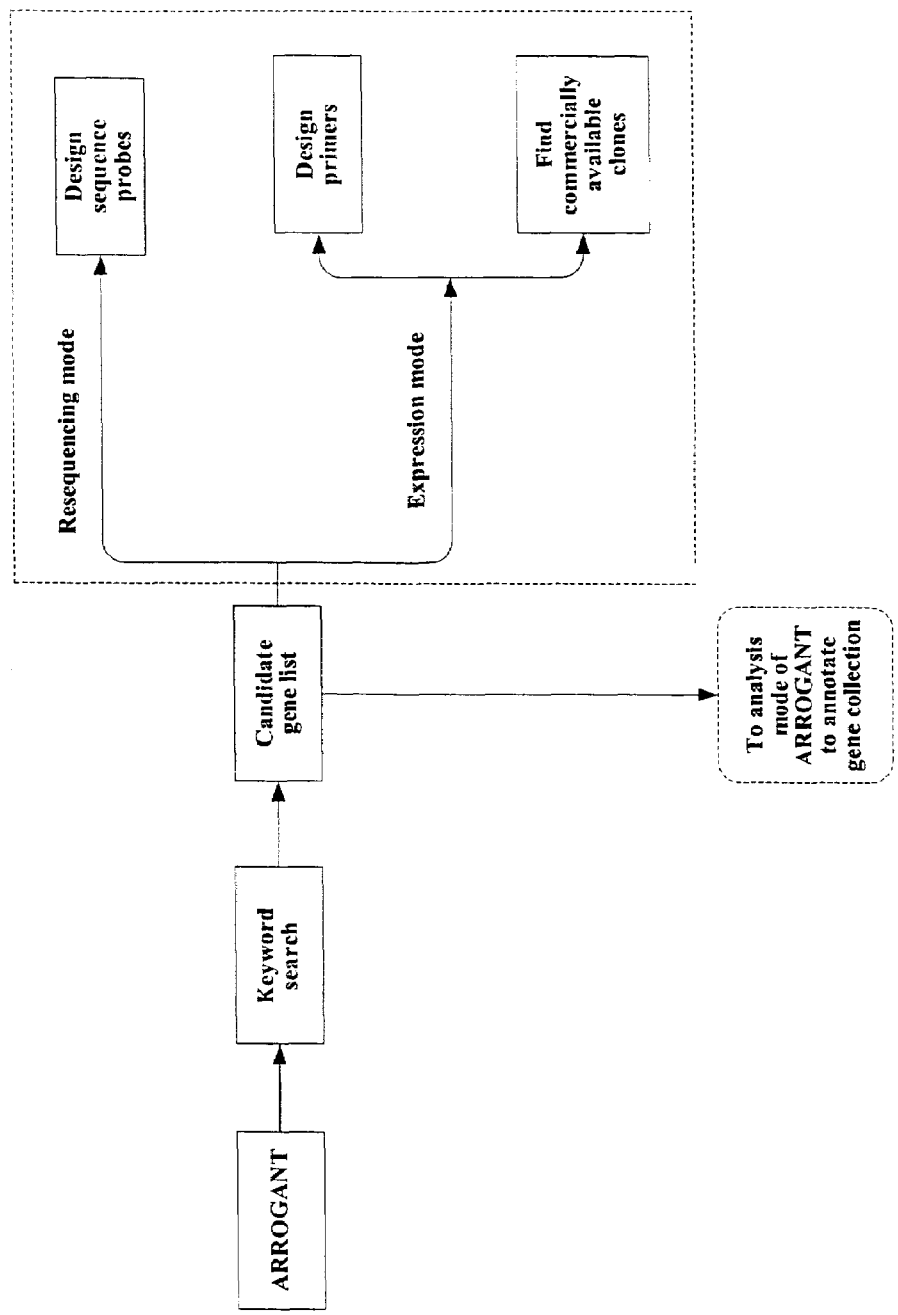
FIG. 5: Block diagram of ARROGANT in design mode.
Figure 6:
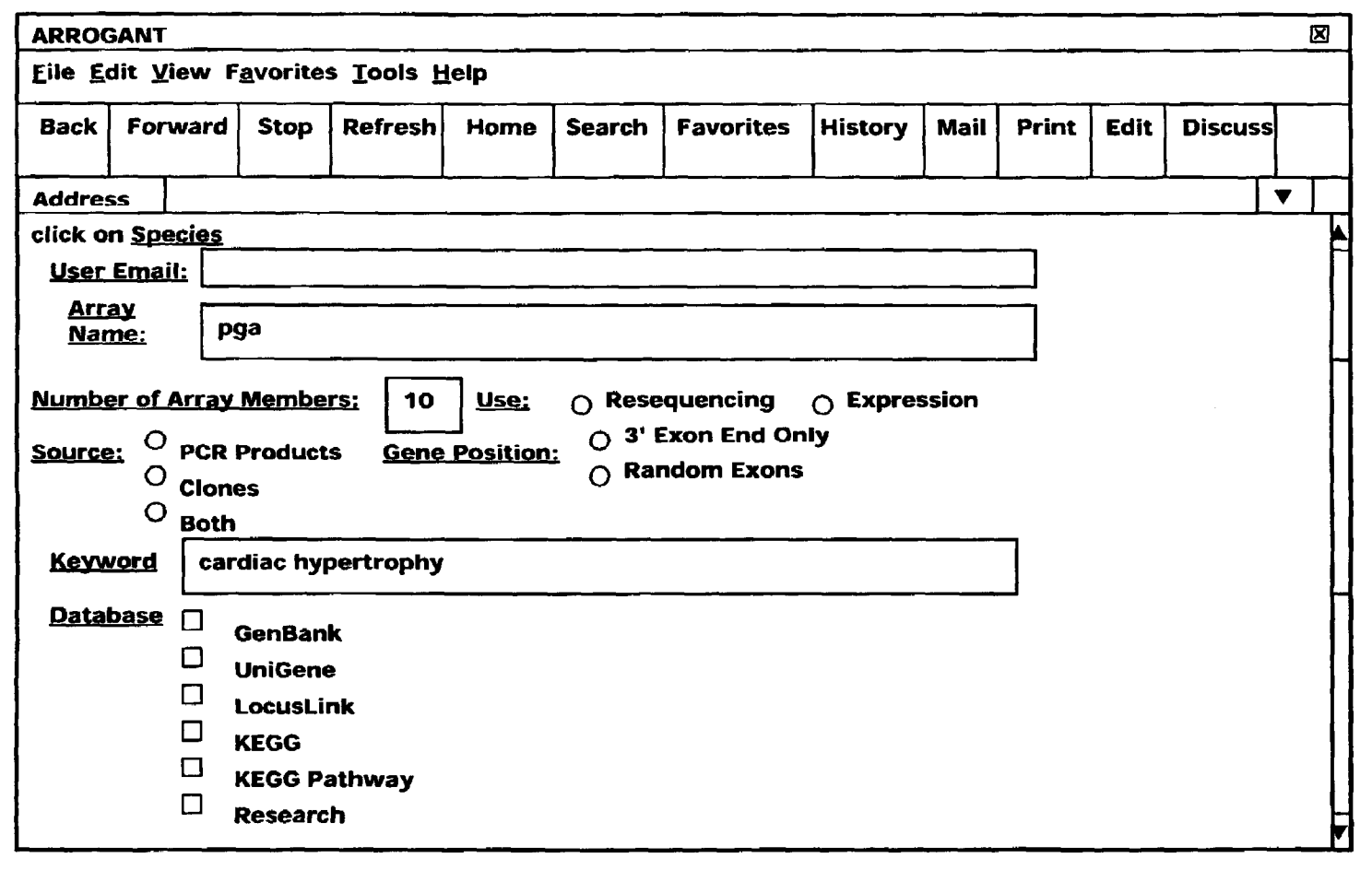

3.5 Design Mode: The intent of the design mode is to let the user look for potential candidates associated with keywords to compile large gene collections and also help in the design of resequencing/expression microarrays. FIG. 5 shows a block diagram of ARROGANT in design mode. The keyword search lets the researcher look for potential candidates in several different databases simultaneously. FIG. 6 shows a snapshot of the input page for the design mode. This page serves to collect the following information from the researcher:

1. Email: Mandatory. Used later to email the results (primers, clones, FASTA files, probes etc.) to the researcher.

2. Array Name: Mandatory. Used for the convenience of the user having more than one array.

3. Keywords: List of Keywords to be searched. Logical operators like 'AND'/'OR' can be used.

4. Select Databases: (At least one must be selected) Multiple databases may be selected at one time; options include: a. GenBank; b. UniGene; c. LocusLink; d. KEGG; e. Research Genetics clone database (<http://www.resgen.com>). Any combination of the above databases may be used.

5. Include File: (Optional). The researcher can add a list of accession number tabs delimited with a floating-point number (any number in general which may indicate priority level, purity of repeat, expression level data, etc.). The 'include file' accession numbers are included in the final list irrespective of whether the keyword search finds it. These accession numbers are added to the list selected by keyword search before proceeding with the next step of designing primers/looking for clones or designing resequencing probes.

3.5.2 Keyword Search: The search is done in such a way that the entries common to different databases are represented only once. Multiple keywords can be used in the search using Boolean operators like AND, OR. e.g. cancer AND aging, klotho OR kl. If no operator is specified then 'and' is assumed. e.g. 'aging klotho' is translated as 'aging and klotho'. The search is case-insensitive. The results are separated into pages and the user can go through different pages using the "Next" and "Back" button or clicking directly on the hyperlink of the page number. The user has the option to select a few entries from the keyword search or enter new keywords and move between pages until he finalizes the gene collection. FIG. 7 shows the sample output obtained by doing a keyword search. The number of entries on each page can be entered by the user.

3.5.3 Fields Retrieved: In general, a unique identifier, a short description and organism are retrieved from each database. Accession number is retrieved as the unique identifier from the research genetics database and all the NCBI databases which include GenBank, UniGene and LocusLink. GenBank numeric identifier (NID) from the KEGG database and pathway number from the KEGG pathway database are retrieved as unique identifiers. The unique identifier from all the databases are hyper-linked to their respective annotation. The output of a keyword search is similar to that obtained on the NCBI website.

3.5.4 Resequencing: Resequencing is done to study the mutations and sequence variation in a DNA sequence. ARROGANT helps in the design of resequencing microarrays by calculating oligonucleotide probes. The Digital Optical Chemistry (DOC) technology may be used to build custom resequencing arrays. The DOC technology uses Digital Light Processors (DLP) chips (Texas Instruments) to create 'digital masks' dynamically. These 'digital masks' are created by directing the light reflected off the DLP. This is possible since every individual mirror on the DLP can be controlled independently. Consequently, the DOC system has the advantage of being able to manufacture custom microarrays for resequencing/expression and the number of array elements can reach 2,000,000. ARROGANT creates a series of probes for each sequence to be put down on the chip for resequencing. The program generates 16 probes of 25 mer after taking different parameters like melting temperature into consideration. This can be directly used by DOC to make the resequencing arrays.

3.5.5 Expression: Expression microarrays are primarily used to study the expression of thousands of genes simultaneously. This technique is very useful if used in different cycles of cell development. Comparison studies involve studying the expression of thousands of genes from normal and pathological subjects. Different color dyes are used to differentiate between the normal and pathological samples. Genes behaving differently are usually studied further. In the case of expression studies, typically clones or PCR products representing a particular gene sequence are spotted down. Our lab also has the spotted microarray technology to develop expression microarrays. The DNA which is spotted is typically around 0.4 kilobases to 2 kilobases. In the case of expression mode, ARROGANT lets the researcher either look for commercially available clones or design primers to create PCR products.

Figure 8:
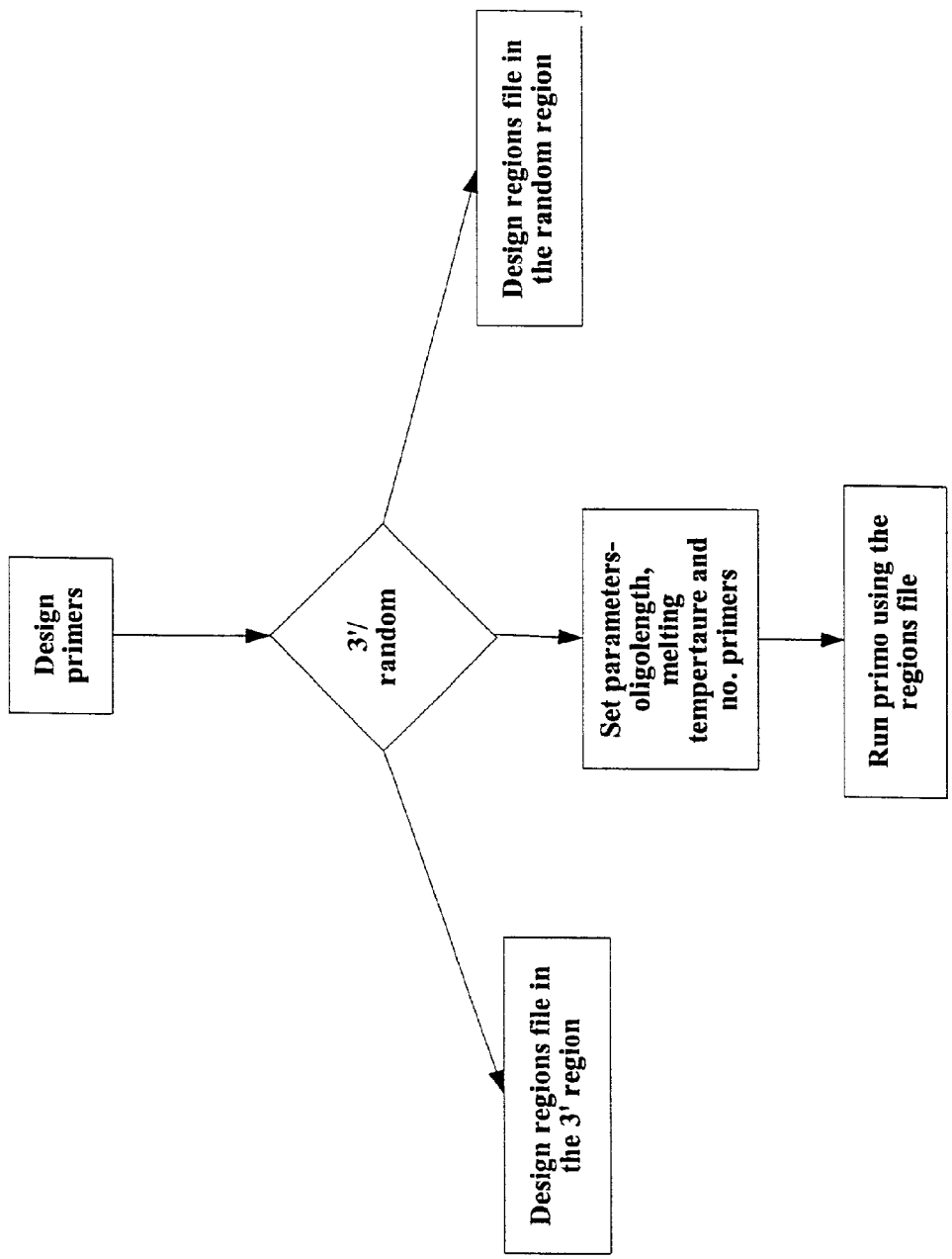
FIG. 8: Flowchart for primer design.

3.5.6 Design of Primers: ARROGANT uses a code called PRIMO available at <http://atlas.swmed.edu>. The code has been successfully used to design primers for a large number of PCR reactions. PRIMO uses a 'regions' file to design primers and amplify the specified region of interest. ARROGANT creates the 'regions' based on the user's selection to design primers either in the 3' or random region. ARROGANT lets the user modify the parameters used for the design of primers. The parameters include: 1. Oligo length: Length of the primer to be designed which is typically around 20 bases. 2. Tm: Melting temperature to be used for PCR reactions. 3. Number of primers to select (per direction): Number of forward and reverse primers to select (default=1). FIG. 8 shows a flowchart for primer design.

3.5.7 Commercially available clones: A database of clones available with Research Genetics has been implemented. The UniGene cluster identifier is first obtained for each sequence and this identifier (instead of GenBank accession/nid) is used to search for clones. The advantage of using UniGene identifiers is that it represents the cluster and all accession numbers belonging to it. This avoids redundancies. This approach eliminates the possibility of getting different clones for the same gene represented by separate accession numbers. Research Genetics provides its own software called CMiner to find available clones. Results of CMiner have been compared to ARROGANT and found to be the same.

3.6 Analysis Mode: The intent of the analysis mode is to annotate a large gene collection and display the annotation table in a format conveneint for the user to view.

Figure 9:
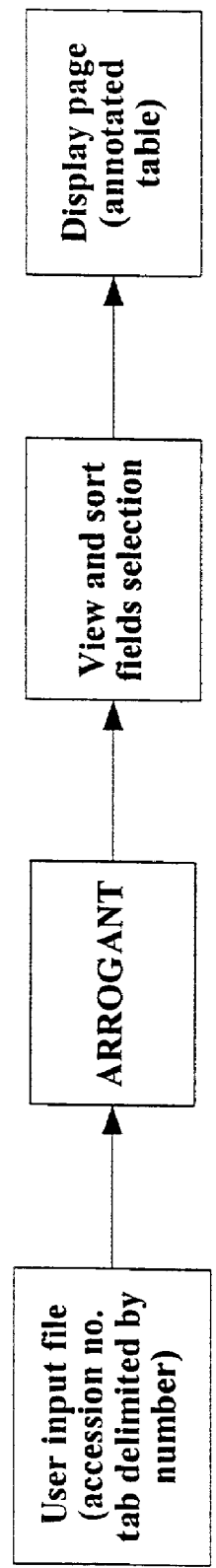
FIG. 9: Block diagram of ARROGANT in analysis mode.

3.6.1 Block Diagram: ARROGANT accepts a list of accession number tabs delimited by a floating point number. Using the various databases implemented locally it annotates the list of accession numbers with 36 different items of information. FIG. 9 shows the block diagram of ARROGANT in the analysis mode. The researcher then has a choice of selecting the fields he would like to view. The researcher can also choose the fields on which the output table is to be sorted. The researcher can sort and sub-sort based on five different fields at one time. FIG. 10 shows the 36 different items of information to choose from and also the five different choices the user has to sort and sub-sort the table.

The input page consists of the following fields:

1. Email: Mandatory. The link to the results page (generated after the analysis mode is completed) is sent to the user.
2. Array Name: Mandatory. Used for the convenience of the user having more than one array.
3. Include File: Mandatory. The user can add a list of accession numbers tab delimited with a floating-point number to input a list of accession numbers to be analyzed.

A count of number of entries found for each field is provided where the data from the first sort column becomes "Not found/Unknown". An additional summary is also provided at the end of the table. For example, consider that the annotation table was first sorted based on 'Homolog' field. At the point when the homologs are not found there would be a summary of a count of entries for each field and also at the end of the annotation table. So if the user would want to do a mouse 'knock-out' experiment he would have a summary of a count of each field for only the ones having homologs. FIG. 11 gives the snapshot of the output display page in the analysis mode.

3.6.2 Fields Retrieved: ARROGANT in the analysis mode annotates each entry in a gene collection with 36 different items of information. The following section explains the significance of each field and its source of retrieval.

Figure 12:
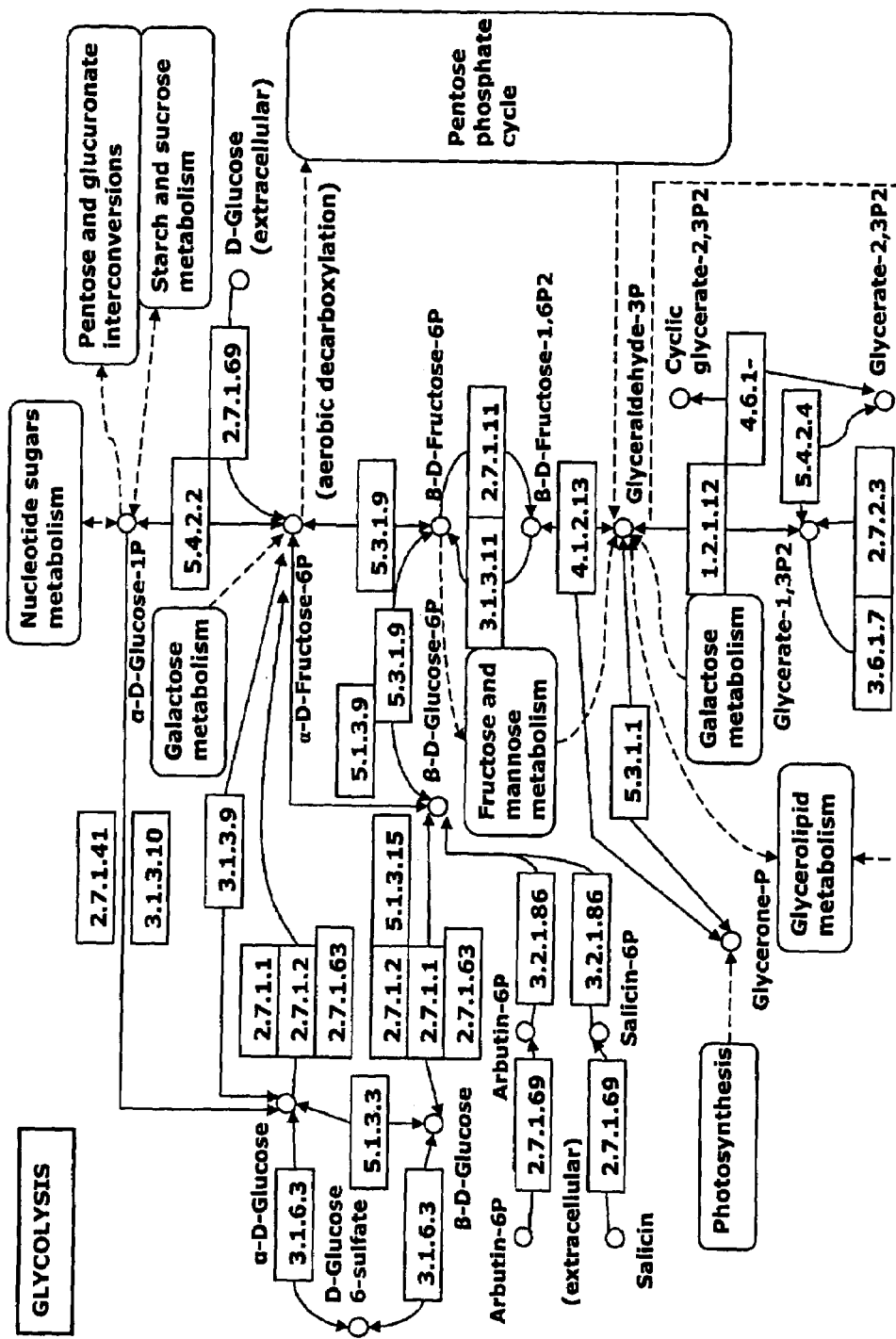
FIG. 12: Example output of Pathways.

1. Accession: The accession number is the most widely used identifier to represent sequences. Accession numbers do not change even if information in the record is changed at the author's request. Consequently, accession numbers are used to input the list of gene collection to ARROGANT. Examples: NT_123456 (constructed genomic contigs); NM_123456 (mRNAs); NP_123456 (proteins); NC_123456 (chromosomes).
2. Unique Identifier (NID): "GenInfo Identifier" (GI) is another sequence identification number used by GenBank. If a sequence changes in any way, a new GI number is assigned. ARROGANT retrieves NID for each GenBank accession number, e.g. 4557722.
3. Related Sequences: All sequences belonging to the UniGene cluster of the current entry are considered related and retrieved. Related sequences are obtained from the NCBI UniGene database.
4. Taxonomy: Taxonomy of the organism to which the given sequence belongs is obtained from NCBI GenBank database implemented locally.
5. Repeat: Potentially polymorphic repeats for the given sequence cluster are identified. This is retrieved from the output generated by our code Rep X.
6. Hairpin/Palindrome: Hairpins and Palindromes are found in the sequence by Rep X.
7. Homology: HomoloGene (Zhang et al, J. Comp. Biol. 2000) database is used to find homologs/orthologs. UniGene identifiers are used to represent the whole cluster. HomoloGene database calculates homologs by nucleotide sequence comparison between all UniGene clusters for each pair of organisms. Homology information might be useful for 'knock-out' experiments.
8. Research Genetics Clone ID: The researcher might want to know wheather a clone is commercially available for a given sequence. ARROGANT outputs clone identifiers available with Research Genetics. The clone query is done using its corresponding UniGene cluster identifier.
9. IMAGE: ARROGANT also lets the researcher retrieve information about whether a clone can be obtained from the IMAGE consortium.
10. Cross Hybridization: This field is specific to using ARROGANT for expression profiling microarrays. An artifact sometimes observed in the results obtained from an expression profiling microarray experiment is that some sequences might hybridize to other sequences to which they are significantly similar. ARROGANT points out the potential cross-hybridizing candidates due to regions of sequence similarities. It tags the potential candidates and lists a score of the total false signal expected and the corresponding cross-hybridizing genes. This information can also be used by the researcher to design primers so as to exclude the regions causing cross-hybridization.
11. cDNA Source: Determines the source of DNA for the particular sequence. It is obtained from the "cDNA Source" tag of UniGene. This helps the researcher know the possible places where the gene was found to be expressed.
12. GDB ID: The Genome database is an important resource used to retrieve information about a sequence. ARROGANT retrieves the GDB identifier and hyperlinks the identifier to its original source. This is obtained from LocusLink database.
13. Gene Name: A given sequence can have a number of different gene names. ARROGANT retrieves the official gene names for a particular sequence or of the UniGene cluster to which it belongs. Retrieved from UniGene as the 'Gene' tag, LocusLink as the 'Official Gene Name', Genome Database as 'Description' tag and the KEGG database as the 'Name' tag.
14. Expression Data: This is an additional field entered with the accession numbers, which could represent expression level data/log expression value (for microarray data), purity of repeat (polymorphism studies), priority of genes on the list or order of genes on the list. The expression level data can be a number anywhere from 0.00001 to 1000000.
15. Gene function: ARROGANT provides a short summary of the function or description of the sequence/cluster of the current sequence. This is retrieved from UniGene as the 'Title' tag and from LocusLink as the 'Summary' tag. This helps the researcher to get an idea of the possible function for a given sequence.
16. Synonyms: A list of symbols and names used for a given gene sequence. It is retrieved from LocusLink as 'Official Symbol' tag. This can be used by the researcher to identify all the names/symbols associated with the given sequence. These could be further used for a keyword search.
17. Pathways: Pathways that the gene sequence might be involved in. It is retrieved from the KEGG database. FIG. 12 shows an example of a pathway displayed by ARROGANT. The pathway information can help the researcher deduce important inferences. For example in a microarray studies, the expression level data when correlated with pathways can help include new genes in a pathway or associate new pathways with diseases and phenotypes.
18. SNP: Single Nucleotide Polymorphism records for a particular sequence are retrieved from the LocusLink database. This might help associate mutations with specific pathological conditions.
19. Title: Brief description of sequence obtained from GenBank database which includes information such as source organism, gene name/protein name, or some description of the sequence's function (if the sequence is non-coding).
20. PubMed: Provides a link to the various articles and journals related to the sequence from the PubMed database. PubMed entries are retrieved from LocusLink database. This helps the researcher view an abstract of the article describing the function of the particular gene sequence.

21. Reviewed RefSeq: ARROGANT outputs reference sequences based on their LocusLink cluster. This helps eliminate different accession numbers representing the same gene.

22. UniGene ID: Represents the identifier of the UniGene cluster to which the given sequence belongs. The UniGene identifier is further linked to its UniGene annotation which can be a useful source of information to the researcher.

23. LocusLink ID: Represents the identifier of the LocusLink cluster to which the given sequence belongs. This is again hyperlinked to its LocusLink annotation. Many researchers might frequently want to convert their lists from one identifier to another. Using the annotation mode of ARROGANT, accession numbers can be converted to LocusLink, UniGene, and KEGG identifiers.

24. Alias Symbol: ARROGANT lists alias symbols used for a given gene sequence. They are retrieved from LocusLink using Alias Symbol tag.

25. Alias Protein: ARROGANT lists alias proteins for a given gene sequence. They are retrieved from LocusLink using 'Alias Protein' tag.

26. Phenotype: Phenotypes found and associated with mutations in this gene. They are obtained from the LocusLink tag 'Phenotype'.

27. Phenotype ID/OMIM ID: For humans, this represents OMIM (Mendelian Inheritance in Man) number. They are retrieved from LocusLink as 'Phenotype ID' tag.

28. Map Location: It indicates the location of the gene on the chromosome map. Map location is retrieved from the 'Map' tag of LocusLink and also from its UniGene entry.

29. Map Link: Provides a link to the graphical representation of the gene on the chromosome. This again is retrieved from LocusLink-'Map' tag.

30. Map Type: Map-Type is the type of map information (G=genetic, C=Cytogenetics). This also is retrieved from LocusLink-'Map' tag.

31. STS—Markername: STS are sequence tag sites, which are short sequences that are operationally unique in the genome, used to generate mapping reagents. It is retrieved from the STS-Markername tag of LocusLink.

32. STS—Chromosome: Retrieved from the STS-Markername tag of LocusLink

33. STS—ID: Retrieved from the STS-Markername tag of LocusLink

Each item is hyperlinked to the help file which exactly defines what each field means and how it is retrieved.

3.6.3. Sorting: ARROGANT lets the user sort the final output display based on five different fields. The intent is to allow the user to look at the output in a convenient manner. This would help the user to answer questions like 'Which of the genes in this large gene collection have known SNP entries and also have a mouse homolog which could be used for a knock-out experiment?' Consider an example where the researcher has a large gene collection to study polymorphism. The researcher might first group the genes based on their chromosome location by sorting them based on chromosomes. Assume that the user is interested in looking for polymorphic genes on chromosome 3. He could select the second level of sort as repeats which would bring the genes belonging to chromosome 3 and having polymorphic repeats on top of the list. Further the researcher might want to know for how many of these top genes are the pathways known. This can be achieved by selecting the third level of sort as pathways. Thus the user can sort and sub-sort to analyze the large gene collection in a convenient manner.

3.6.4. Add Accession Numbers: ARROGANT lets the user add accession numbers to her already submitted list in the analysis mode. The user has the option of adding more entries to her list while viewing the annotation of her previous list. The new list thus created automatically avoids duplicates and sequence redundancies. This lets the user add more entries to her list assembled earlier. For example, the user could have annotated a list of four thousand genes associated with cancer using the analysis mode of ARROGANT and can add thousands more entries to be annotated and combined with this list years later.

3.7 Merging Gene Collection Mode: In merging gene collection mode, the user could submit two or more lists of genes which could be combined into one unique list avoiding all duplicates. The redundancy is avoided by eliminating accession numbers belonging to the same UniGene cluster. The input page to the merging gene collection mode consists of the following input fields. 1. User Email: Mandatory. The merged gene list and the original gene collection is sent to the user on this e-mail address. 2. Array name: Mandatory. The name to be associated with the gene collection. 3. Input file: Mandatory. Input one file containing sequence redundancies.

Section 4: Implementation

This section deals with the details of the software implementation of ARROGANT. ARROGANT is a database driven software. The section talks about databases implemented by ARROGANT, algorithms used in the design, analysis and the merging gene collection mode.

4.1 Databases: As described, ARROGANT combines results from several different databases. All the databases are implemented in the relational database format in SQL server 7.0. In the following section each database is introduced and its implementation is covered in brief.

4.1.1 GenBank: GetBank, an annotated collection of all publicly available DNA sequences provided by NIH, is the biggest and the most used publicly available database (Nucleic Acids Research 2000 Jan 1;28(1):15–8). There are approximately 10,897,000 sequence records as of February 2001 <http://ncbi.nih.gov>). The complete release notes for the current version of GenBank are available at <ftp://ncbi.nlm.nih.gov/govbank/gbrel.txt>. The GetBank database is the single most important database to search for possible gene candidates, Each GenBank entry has a unique identifier called accession number. ARROGANT uses accession number as its primary key to link different databases. ARROGANT uses GenBank database in design and analysis mode. GenBank is implemented as a separate database on the server called 'geneifliligenebank' to improve the speed perfonnance, as the database is very large containing approximately 10.8 million entries. The database is implemented as a single table, see FIG 13. ARROGANT GenBank database implemented in SQL Server 7.0 does not include the actual sequence for each entry. This is obtained using the NCBI tools implemented locally on our HP/UX computers. A shell script 'getgb' compares files present locally with its original source on the web and downloads only the ones not existing or having a different file size from <ftp://ncbi.nlm.nih.gov/genbank>. The files are unzipped, combined into one huge file, split into smaller files of approximately equal sizes and then reformatted and can then be directly imported into the database using fire 'bulk insert' script.

4.1.2 UniGene: UniGene partitions GenBank EST sequences into a non-redundant set of gene-oriented clusters. Each UniGene cluster contains sequences that presumably represent a unique gene, as well as related infonnation such as the tissue types in which the gene has been expressed and map location. The UniGene database was chosen to be a part of ARROGANT (see FIG. 14) for the following reasons: 1. Avoid Redundancy: ARROGANT uses UniGene database to avoid redundancies by not including sequences having different accession numbers but representing the same UniGene cluster. ARROGANT uses this in the merging gene collection mode to combine different lists into one unique collection. 2. The UniGene database includes gene sequences as well as hundreds of thousands of expressed sequence tag (EST) sequences. 3. Additional Annotation: Provides additional annotation for a given gene sequence, e.g. cDNA source, which is used to look for keywords (design mode) and annotate gene collection (analysis mode). As a result UniGene database is used in all the three modes by ARROGANT. Perl scripts combine similar files (<ftp://ncbi.nlm.nih.gov/repository/UniGene/>) of different organisms together, convert the files into various files of specific format which can be imported directly into the database tables using the import function in SQL Server 7.0.

Figure 15:
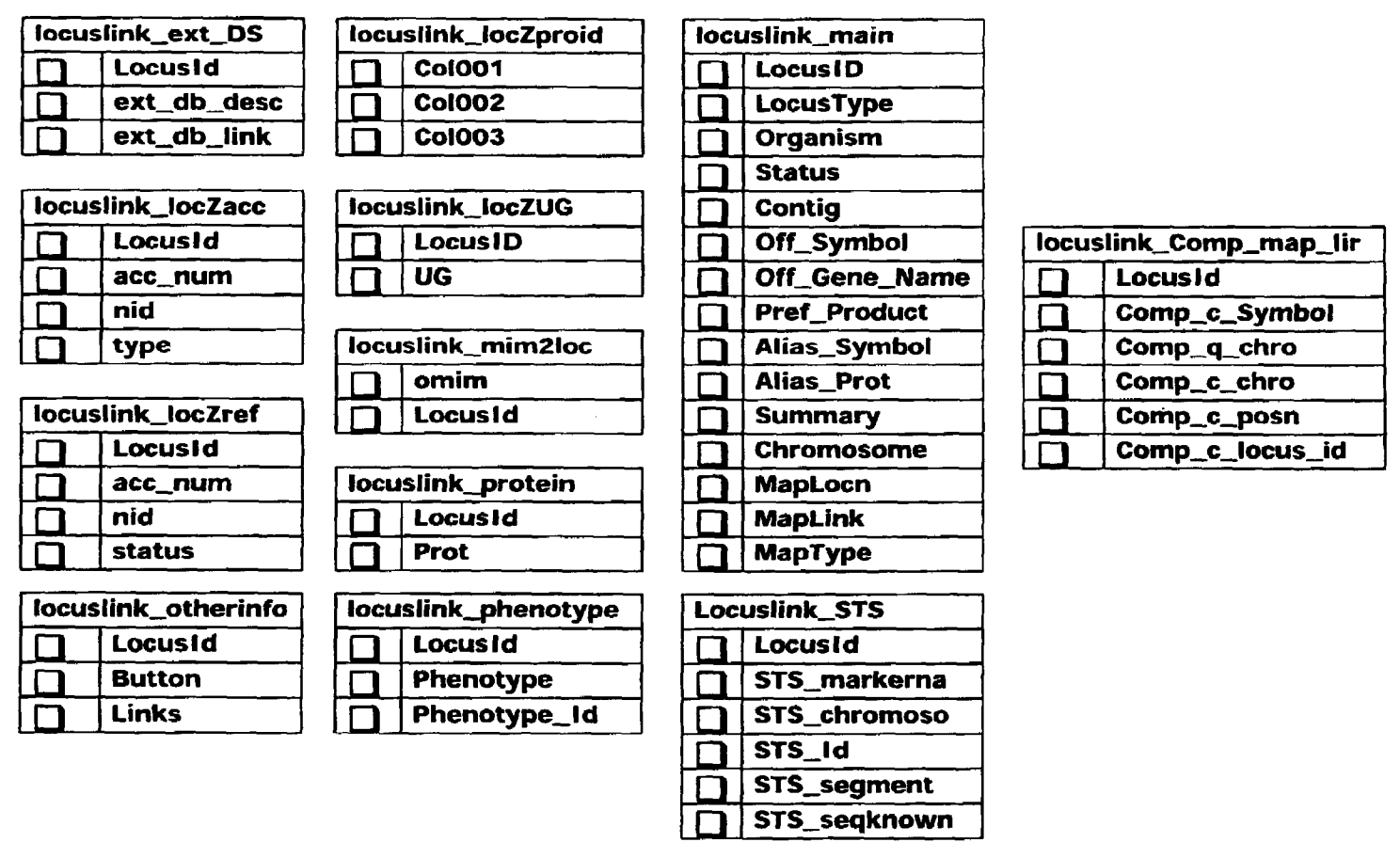

4.1.3 LocusLink: LocusLink is NCBI's attempt to integrate and provide a single query interface to clustered sequences and make available descriptive infonnation about genetic loci. However, LocusLink does not provide annotation to a collection of genes. ARROGANT extends its capabilities by incorporating LocusLink database. Sequence accessions include a subset of GenBank accessions for a locus, as well as a new type, the NCBI Reference Sequence (RefSeq). LocusLink provides a reference sequence for each locus cluster. LocusLink database is used by ARROGANT in the design and analysis mode, see FIG 15. Series of Visual Basic executables import files into the database, downloaded from NCBI (<ftp://ncbi.nlm.nih.gov/refseq/LocusLink/LLt-mpl>).

4.1.4 KEGO Genome and Pathway Database: ARROGANT not only combines different databases from NCBI but also uses the KEGG databases. Kyoto Encyclopedia of Genes and Genomes (KEGG) makes available, information pathways consisting of interacting molecules or genes by using the current knowledge of molecular and cellular biology (Kanehisa, M., Oxford University Press 2000). In addition KEGG database also provides additional annotation used by ARROGANT to look for keywords and annotate gene sequences. As a result KEGG database is used by ARROGANT in both design and analysis mode, see FIG. 16. The files downloaded from KEGG (<ftp://kegg.genome.ad.jp/genomes/genes/>) are combined as one, split into smaller files and the Visual Basic executable is used to update the tables. A file containing additional pathway information is used (<ftp://kegg.genome.ad.jp/pathways/maptitle.tab>).

4.1.5 HomoloGene: The HomoloGene database provides homologs/orthologs, which is used as a field in the annotation of large gene collection by the analysis mode, see FIG 17. It primarily uses the UniGene cluster identifier to search for homologs/orthologs. Accession numbers and LocusLink identifiers may also be used. HomoloGene uses nucleotide sequence comparisons to calculate orthologs and homologs, between all UniGene clusters by each pair of organisms. The HomoloGene database is downloaded from <ftp://ftp.ncbi.nlm.nih.gov/pub/HomoloGene/hmlg.ftp>. Perl scripts format the downloaded file, which is further imported into the database. Special character '^' is used as the delimiter to import the file into the database.

4.1.6 Research Genetics Clone Database: Research Genetics commercially distributes selected clones from the IMAGE consortium. The catalog of clones available at Research Genetics can be downloaded at <ftp://ftp.resgen.com/pub/svlibraries/RGHsseqver101100.txt>. The catalog contains annotation related to the clones like accession number, gene name, cluster ID, insert size, markers, etc. ARROGANT stores this catalog locally in the database, which is used to find commercially available clones and search for candidate genes in the design mode, see FIG 18.

Figure 19:
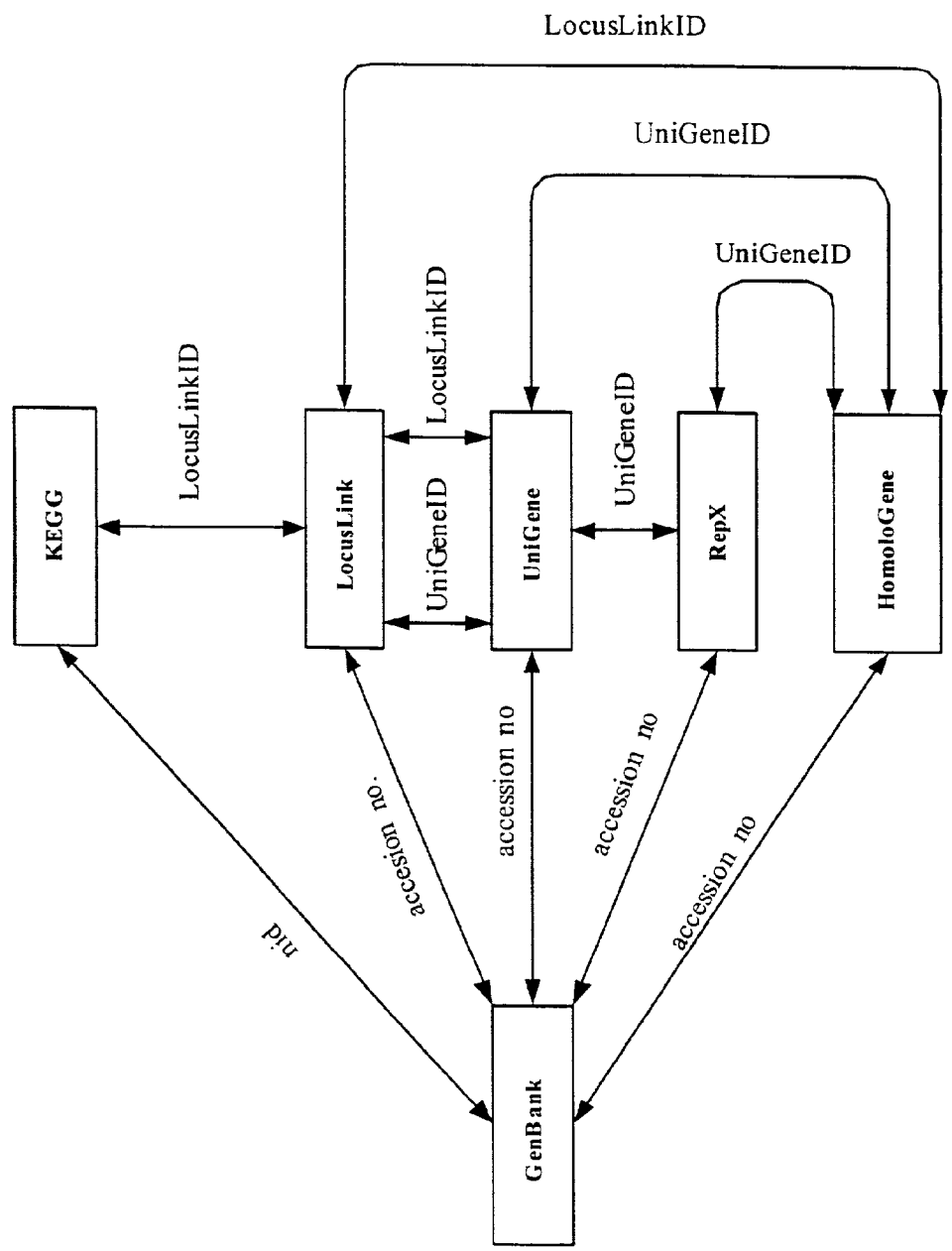
FIG. 19: Relationship across different databases.

4.1.7 Relationship of different databases to one another: ARROGANT facilitates simultaneous keyword searches and annotates gene collections using different databases. This is achieved by implementing all the databases locally in SQL server 7.0 database. As shown in FIG. 19 GenBank database is the only database linked to all other databases. GenBank is linked to KEGG database using NID (Numeric Identifier) and to all other databases by accession number. UniGene and LocusLink databases both contain LocusLink Identifier as well as UniGene identifier. The HomoloGene database is linked to GenBank by accession number, to UniGene by UniGene identifier and to LocusLink by LocusLink identifier. RepX database contains UniGene identifier. The KEGG database is also linked to LocusLink via LocusLink identifier. Thus ARROGANT integrates different databases from both NCBI and KEGG.

Figure 20:
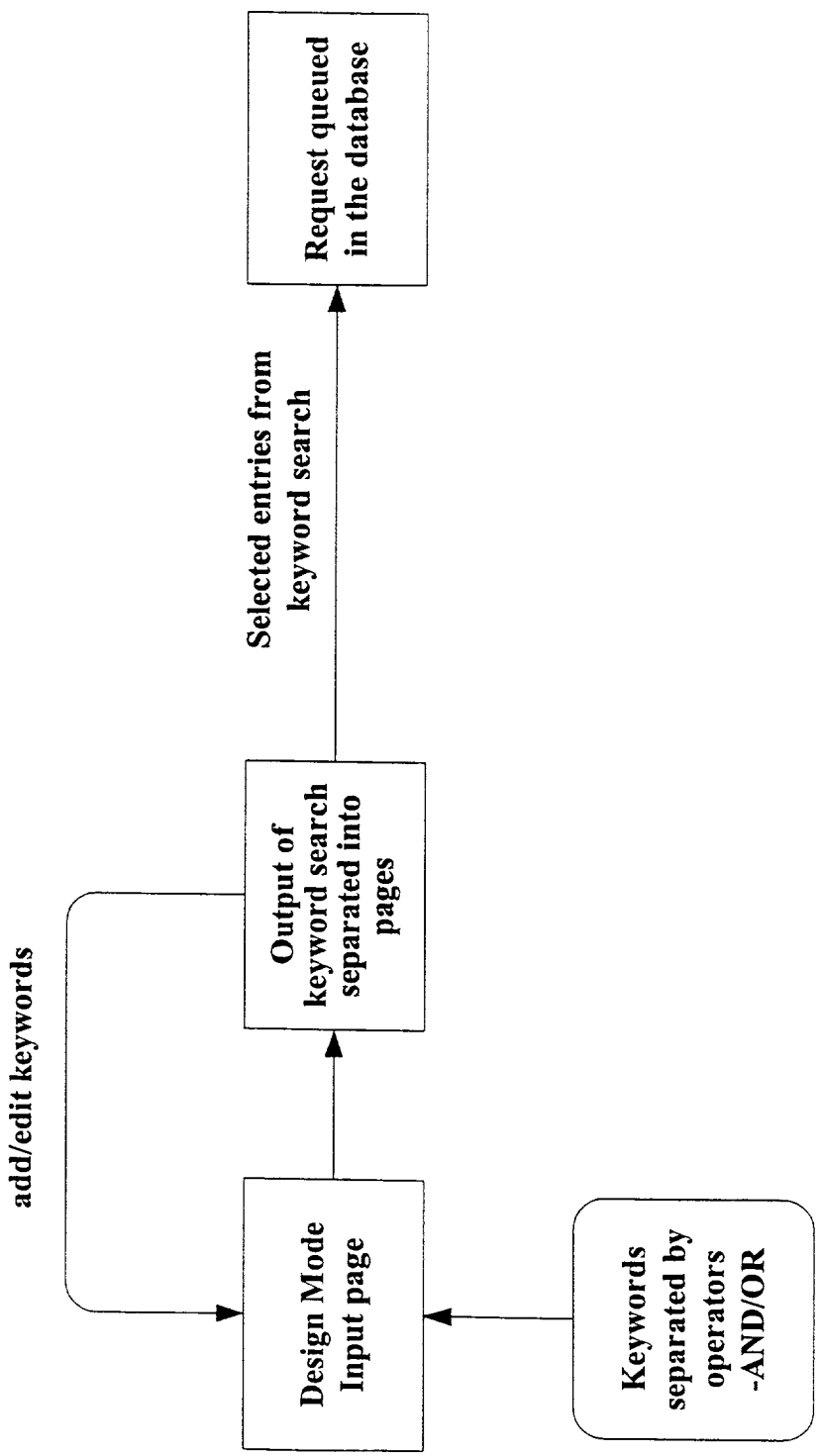
FIG. 20: Implementation of the design mode.
Figure 21:
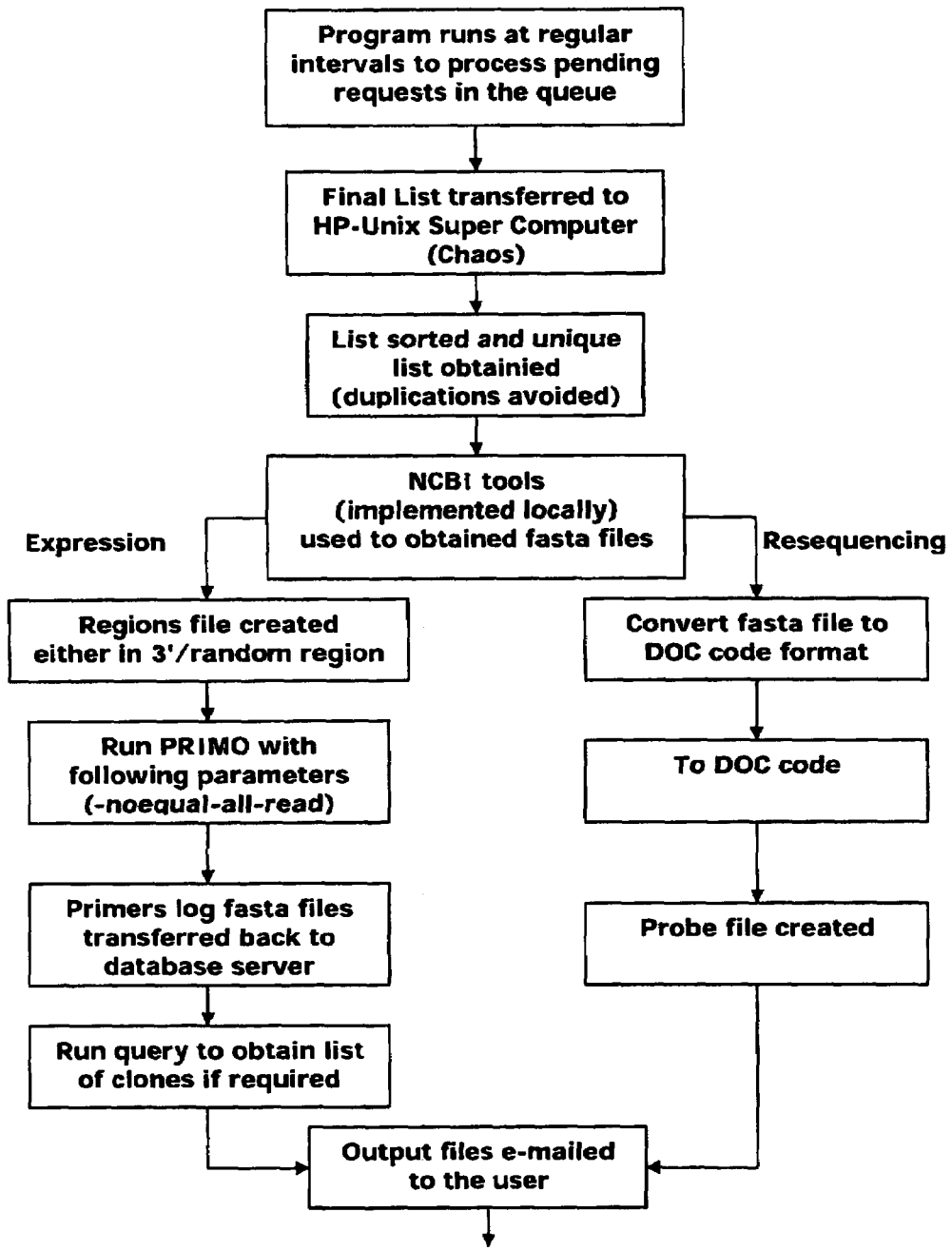
FIG. 21: Flowchart for the design mode.

4.2 Implementation of the Design Mode: ARROGANT in the design mode can be used to find candidate genes using keyword search, and design expression/resequencing microarray. The keyword search can be done online and the selected entries are queued in the database. FIG. 20 shows the implementation of ARROGANT in design mode. Keywords can be entered and databases can be selected in the input page e.g. 'Cancer AND chromosome 3' can be searched in GenBank and LocusLink. The user can select a few genes of interest by going through different pages from the keyword search. Each gene is hyperlinked to its annotation. The user can also input new keywords and select from these new entries to add to the final list. The final gene list is a set of accession numbers/GenBank unique identifiers. The final list is then inserted in a database table and the request is queued. The requests are processed one by one. FIG. 21 shows the flow of events after the request is queued. The list of accession numbers is first transferred to the HP/UX computer where duplicates are eliminated. The FASTA files are obtained for these accession numbers using the NCBI tools (implemented locally), which run on all the NCBI sequence databases to make sure that none of the entries are lost e.g. Human EST sequences, patent sequences, non-redundant sequence database, etc.

After the gene collection is finalized, the user can further use ARROGANT to design expression or resequencing microarray. For expression microarrays the user gets to choose to either design primers and/or find commercially available clones. If the option includes designing primers then depending on the whether the user wants it designed in the 3'/random exon region an appropriate regions file is created. Once the 'regions' file is created PRIMO is run on the combined FASTA file to design primers for each sequence so as to amplify the specified region. The output files are transferred back to the windows terminal. Depending upon the user selection, clone query may run on the list to find out the possible clones. Finally the request is cleared from the database and the user is sent the following attachments: 1. List of GenBank identifiers for genes selected. 2.

Combined FASTA file for all the genes. For expression mode, 3. File containing designed primers for all the sequences. 4. A log file specifying the parameters used for the design of primers. 5. A file containing Research Genetics clone identifiers for clones available with Research Genetics. For resequencing mode, 6. A file containing resequencing probes for all the sequences on the oligonucleotide microarray. This summarizes the algorithm of ARROGANT in design mode. Consequently, ARROGANT in the design mode can be used to compile a large gene collection. For microarrays the design can be further extended to help generate expression/resequencing microarrays.

Figure 22:
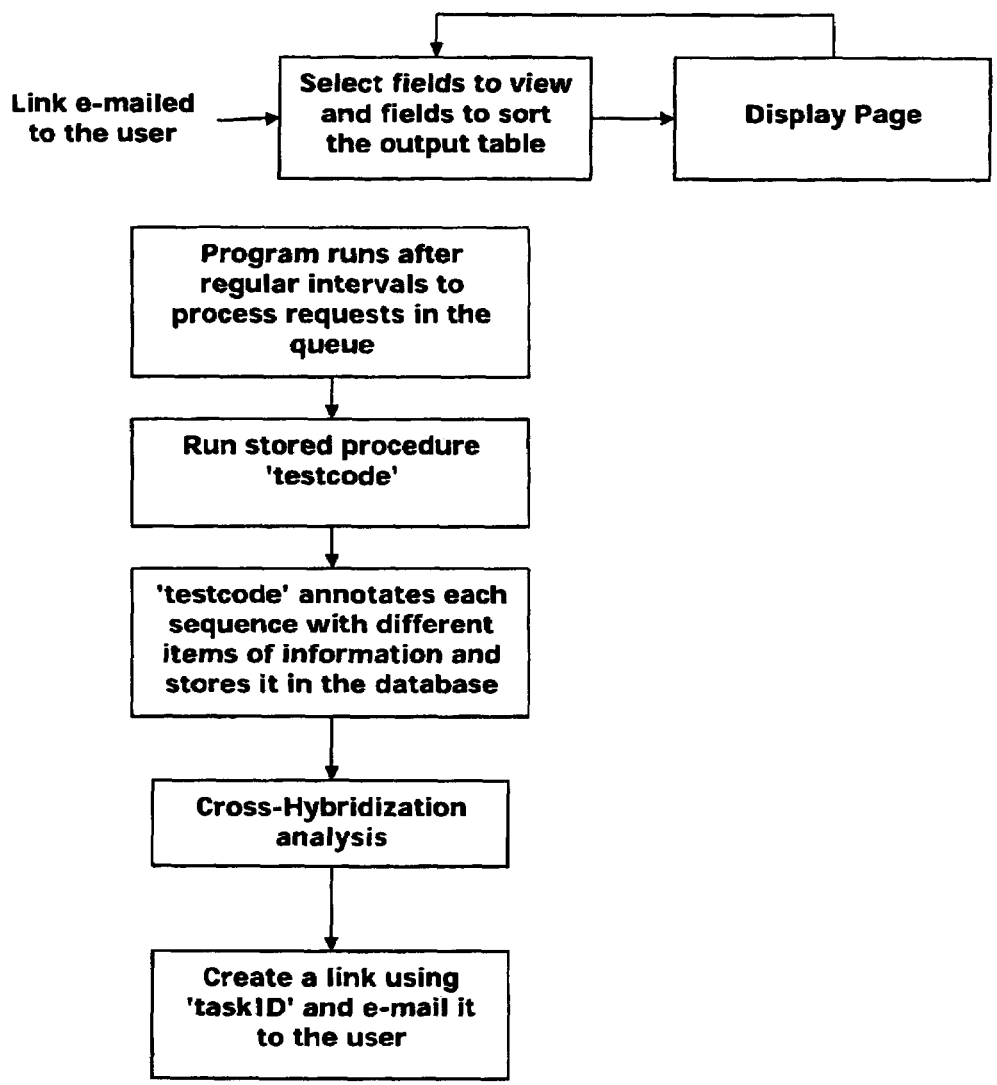
FIG. 22: Implementation of the analysis mode.

4.3 Implementation of the Analysis mode: ARROGANT in the analysis mode, is intended to be an annotation tool for large gene collections. The following section describes the user interface and the algorithm used in the analysis mode. FIG. 22 summarizes the working of ARROGANT in the analysis mode. The list of accession numbers is first stored into the database table and the request is queued. The queue is processed one by one. The processing begins by running a stored procedure called 'testcode' which pulls the different fields of annotation related to the sequence as listed in the earlier section of block diagram description. ARROGANT then proceeds to estimate the amount of cross-hybridization possible within the chip and with the entire UniGene database as described in section 3.3. The results related to all the fields on the array are stored in a database and a link unique to the current array is generated using its taskid. This link is emailed to the user. Thus the user could click on the link and access her collection of genes. The user can further add more accession numbers to her collection by using the 'Add Accession' option on the final display page.

Figure 23:
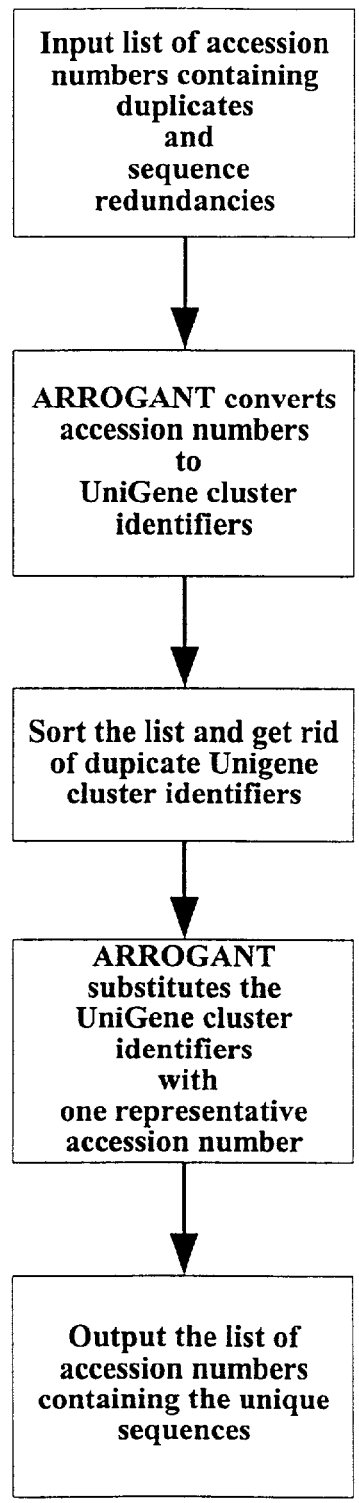
FIG. 23: Implementation of the merging gene collection mode.
Figure 24:
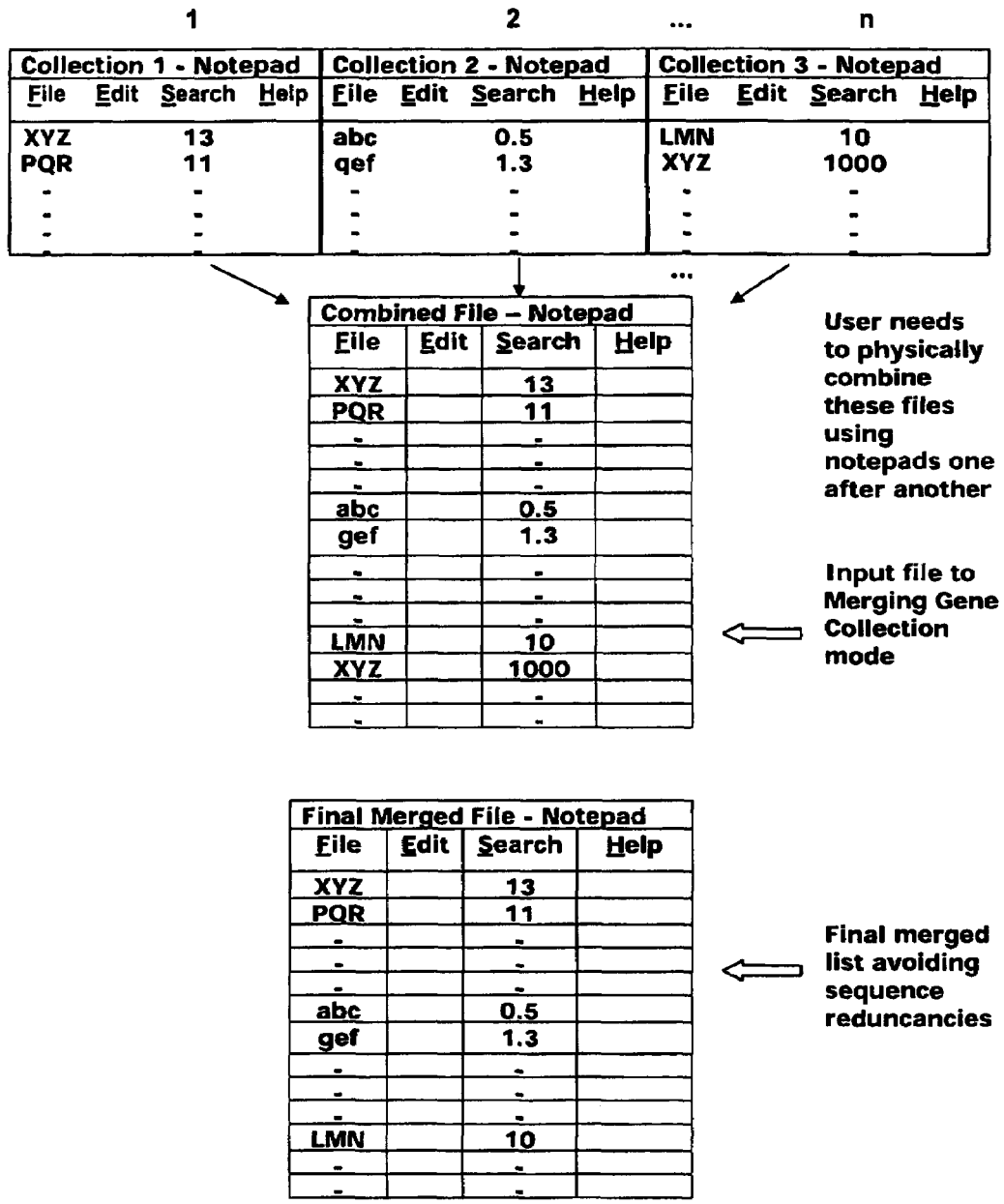
FIG. 24: Input for the merging gene collection mode.

4.4 Merging gene collection: The intent of this mode is to combine genes from different collections/microarrays into one unique list. The duplicates are avoided by first converting the accession numbers to their corresponding UniGene cluster identifiers and then retaining the ones which are unique. FIG. 23 shows the algorithm used to merge different gene collections. FIG. 24 shows the steps need to be taken. The user needs to first combine all the gene collections in one file. This is the input to the merging gene collection mode and the output contains only the unique ones.

4.5 Tools for maintaining the databases: Tools have been developed to maintain the various databases used by ARROGANT. The tools include various Visual Basic executables and perl scripts which either directly update the database or create a file which can be directly imported into the database. The update of each individual database is described in its implementation section. The databases are maintained in a semi-automated fashion. The person in-charge of maintaining the program has to run scripts and later inspect the lock files to verify that the databases were updated properly. This is usually done every fifteen days.

Section 5: Applications

Figure 25:
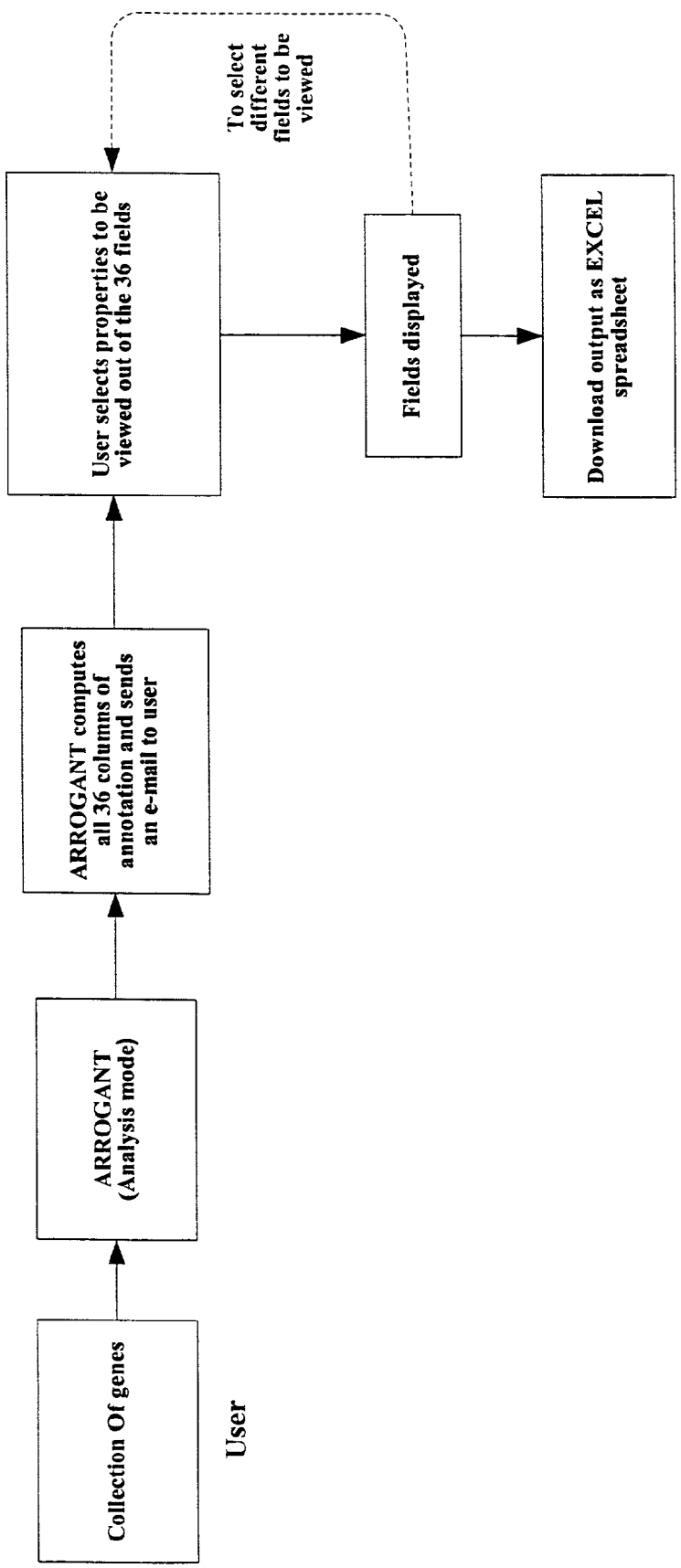
FIG. 25: ARROGANT retrieves sequence properties

ARROGANT provides a useful tool for working with a large collection of genes and for design and analysis of microarrays. In addition, ARROGANT may be used in a wide variety of other applications:

5.1 Retrieve properties to annotate large gene collections: Several different databases implemented locally enable ARROGANT to annotate any given sequence. In the analysis mode, ARROGANT accepts a list of accession numbers from the user and annotates it with 36 different items of information. This is the only tool which annotates a large number of genes simultaneously and presents the data in a tabular format. The table can be downloaded locally and stored on the computer without having to follow any hyperlinks. FIG. 25 summarizes the role of ARROGANT to retrieve properties for a large gene collection. For example, consider a researcher needing to know the chromosome location and the UniGene cluster identifiers for a collection of genes. As long as the list consists of only a small number of genes (less than 30–40) she could do it manually by searching for individual genes on the web. With the recent advancements in technology and the completion of the Human Genome Project researchers are now dealing with hundreds and thousands of genes. ARROGANT offers unprecedented value for retrieving such gene properties for large gene collections.

ARROGANT provides a tool of choice for many users wanting to annotate their large gene collection and have the information stored locally on their computer. This is the only tool the researcher needs to use in order to annotate completely a large list of gene collections. This saves the researcher from exploring multiple different websites and trying to compile all the information, which becomes practically impossible as the number of genes in the list increases. The details of each field used for annotation are described above.

Figure 26:
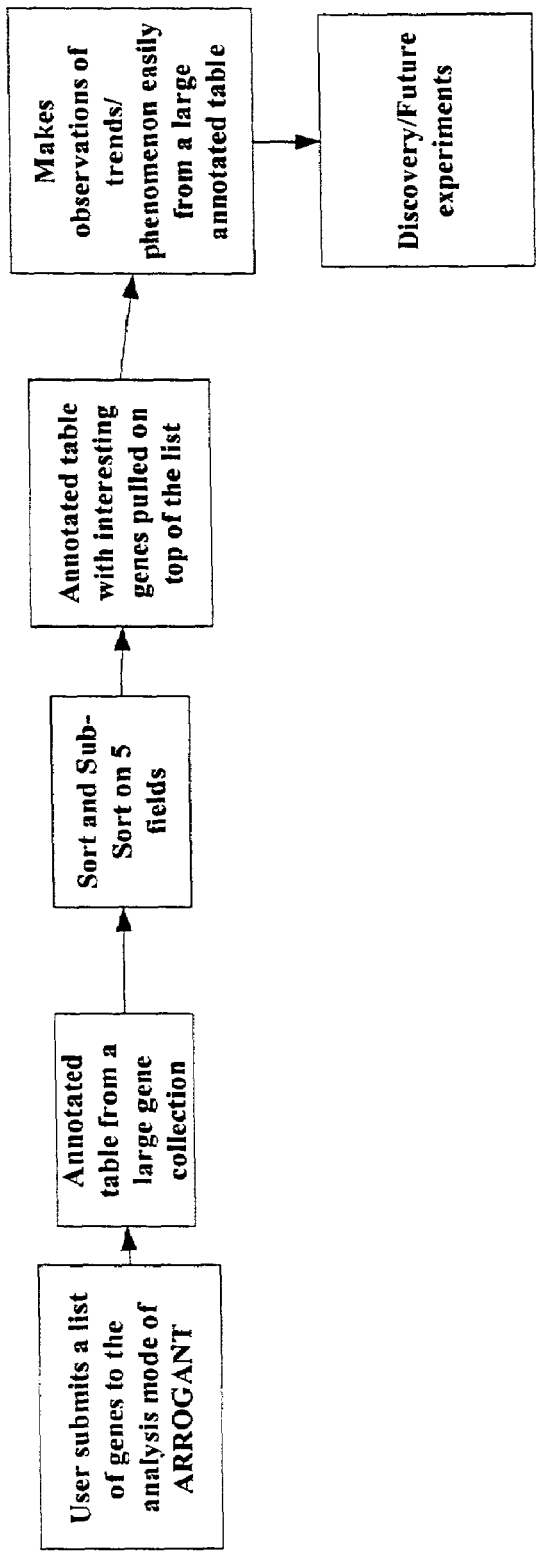
FIG. 26: ARROGANT sorts annotation table

5.2 Discovery Tool: ARROGANT, when used in the analysis mode makes it easier for the user to generate biological inferences and recommendations for future experiments by enabling the user to view a large number of items of information, sorted based on multiple different fields. When used for microarrays, the analysis mode of ARROGANT associates the given gene sequence with 36 different items of information. The user can also overlay a floating point number associated with each sequence which may be expression level data (microarrays), priority level, purity of repeats (for polymorphism studies), etc. The use of ARROGANT in assisting discoveries can be illustrated with an example. Consider the user has entered her gene list with the expression level data in the analysis mode. After selecting the fields to be viewed, there are five levels of sorting available to the user. The user can view the genes expressed highly on top of the list by first sorting on expression level data. Further to get an indication of the genes expressed highly and belonging to a common pathway the second level of sort could be chosen as pathways. So if out of the ten highly expressed genes eight belong to a common/related pathway, and pathways for the remaining two were unknown, then it might indicate that the remaining two belong to the same or related pathways. In this way ARROGANT can help answer questions like 'How many genes that expressed more then 5 fold and having polymorphic repeats also have a mouse homolog which could be used for further knockout experiments?' which can be achieved by sorting on expression data, repeats and homologs. This is easily possible because the various items of information are in one place and the data can be sorted in various ways to filter the interesting ones on top of the list. FIG. 26 illustrates the use of ARROGANT to assist discoveries.

Figure 27:
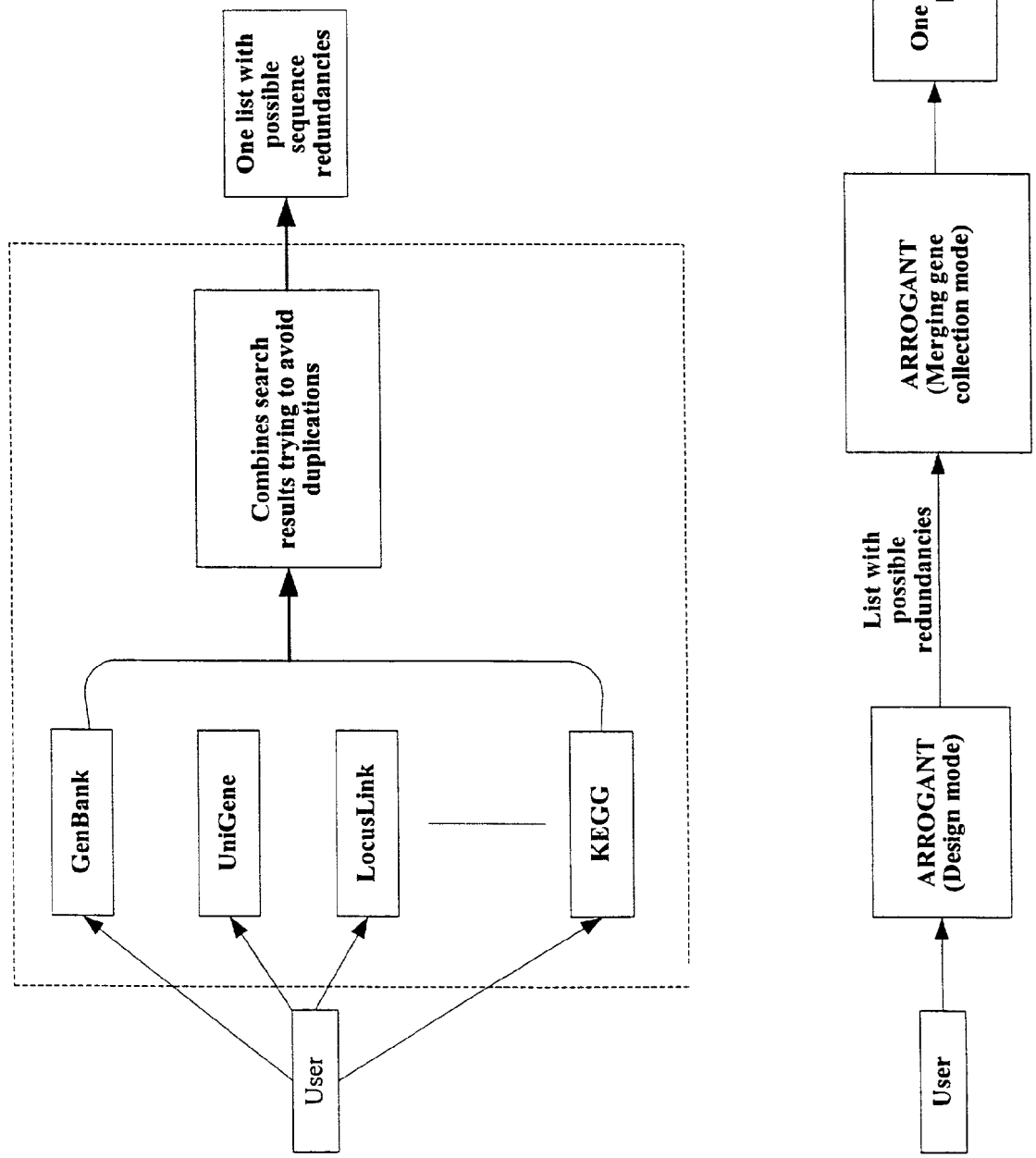
FIG. 27: ARROGANT compiles unique list

5.3 Compile a gene collection: keyword search, avoiding redundancies and duplicates. The merging gene collection mode can be used in combination with the keyword search to compile a unique collection of genes. FIG. 27 shows how ARROGANT helps the researcher in compiling a gene collection. ARROGANT permits surfing through several different databases at one time. A parent schema of all these different databases has been implemented which lets the researcher select the various databases in any combination for a keyword search. This eliminates the need for the user to compile several different lists obtained from many different databases and trying to compile one unique list of genes. ARROGANT also avoids sequence redundancies by allowing only one gene per UniGene cluster. The keyword search can be done using logical operators like 'AND/OR', e.g. 'klotho or kl', 'aging and telomerase'. With the merging gene collection mode, the user can also chose to include an additional list of accession numbers of her genes (in addition to that obtained from the keyword search) to be included irrespective of whether the keyword search finds it, and a unique list is compiled automatically to avoid duplicates.

Figure 28:
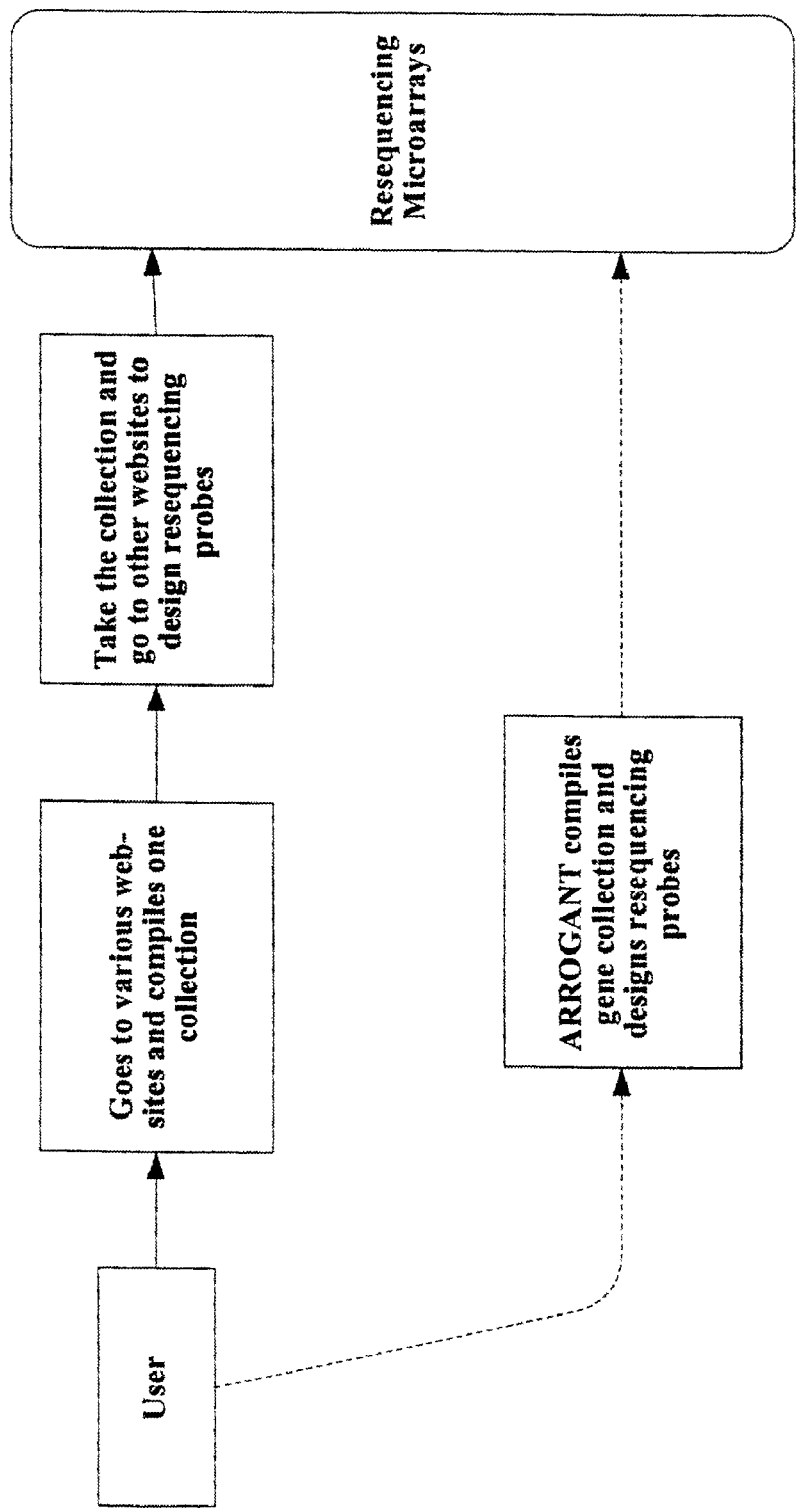
FIG. 28: ARROGANT uses array elements to design probes

5.4 Design of oligonucleotide probes for resequencing: ARROGANT provides the user the unique facility of designing probes after selecting the list of genes using a keyword search and/or adding genes from her own list. The probe design software has been tested and implemented for more than two years in our laboratory. The probes designed have been used to develop chips using DOC (Digital Optical Chemistry) technology developed in our laboratory. For each gene 16 probes of 25 mers each are designed taking parameters like melting temperature, oligo length etc. into consideration. FIG. 28 illustrates how ARROGANT can be used to select members and to design oligonucleotide probes for resequencing arrays. Thus ARROGANT serves as a handy tool for design of resequencing arrays. The design includes selecting unique elements on the array (relevant to the topic of study) and designing probes to represent the sequences on the array.

Figure 29:
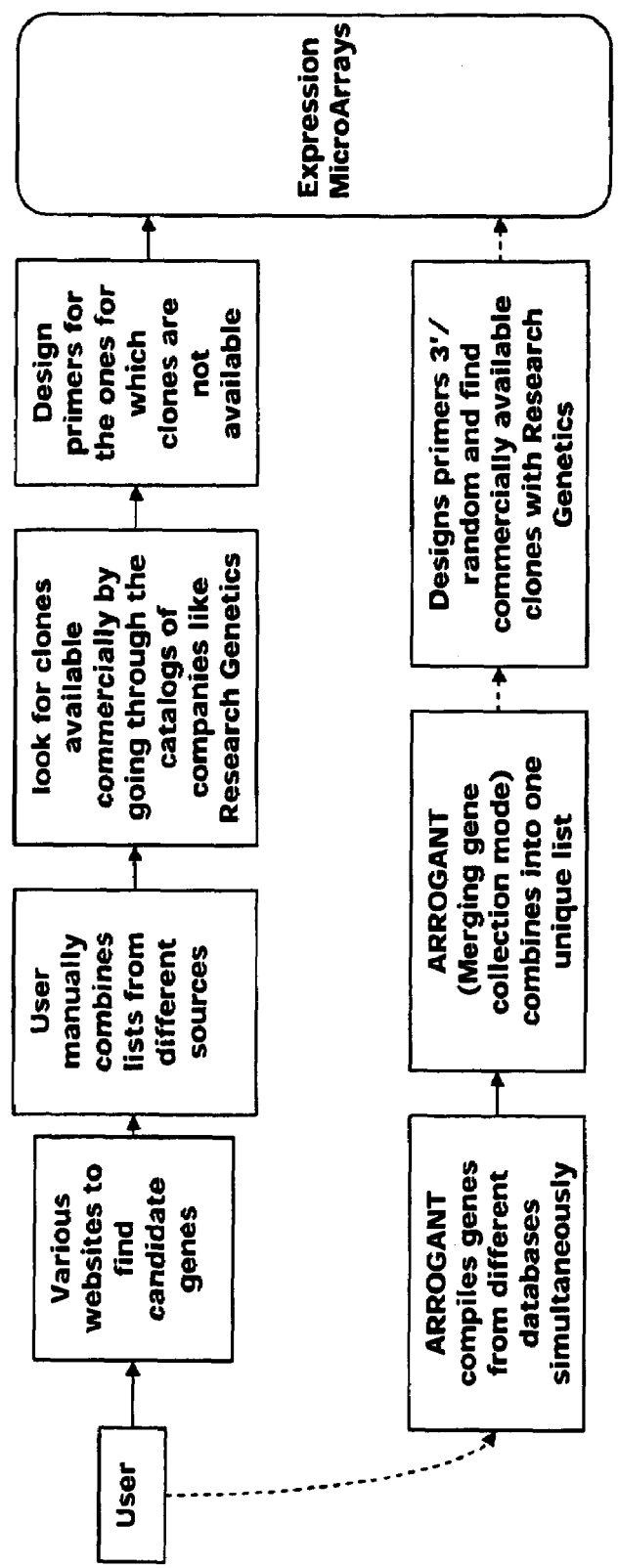
FIG. 29: ARROGANT automates the selection of array elements

5.5 Design of expression microarrays: Expression microarrays often have elements of around 0.4 Kb–2 Kb length spotted; typically, they are either PCR products or clones commercially available. As shown in FIG. 29, ARROGANT automates the selection of elements to be spotted on the array by first looking for possible elements by doing a keyword search and then for the ones selected, the user can either chose to design primers or to look for commercially available clones or both.

5.5.1 Design of Primers: ARROGANT also automates the process of design of primers after selection of the sequences. The design of the primers can be made either in the 3' region or random exon region. Depending on the user selection, the 'regions file' which specifies the region for the design of primers is done so as to select the 3' region or random region. PRIMO (supra) designs primers based on the regions file and the conditions mentioned in the criteria file. The conditions for the design of primers can be modified by changing the criteria file. Oligo length, melting temperature for PCR and number of primers in each direction can be edited by the researcher.

5.5.2 Commercially available clones: ARROGANT lets the researcher look for commercially available clones from Research Genetics, Inc. (Huntsville, Ala.). This can be done either by submitting the list of genes in the analysis mode and then selecting the Research Genetics clone column from the list of annotation. The researcher can also use the design mode of ARROGANT to look for clones by choosing the expression microarray design. The results obtained have been compared to the output of CMiner (Research Genetics, Inc.) and results have been found to tally.

Figure 30:
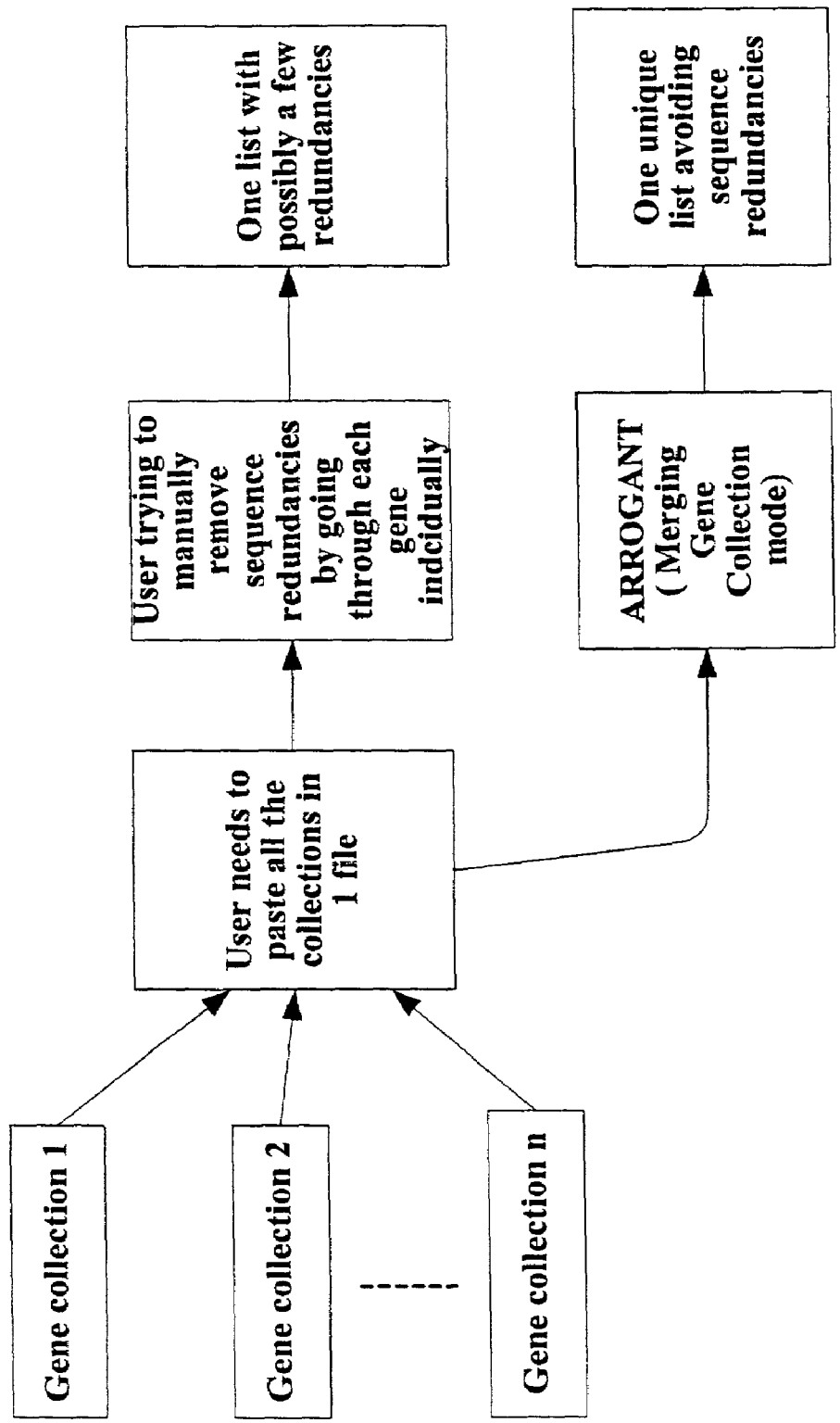
FIG. 30: ARROGANT eliminates sequence redundancies

5.6 Merging gene collections: In the merging gene collection mode the user has the opportunity of combining several different expert list of genes and obtain one unique list. For example consider that the researcher has three separate gene collections related to studying cancer. The first list might have been obtained by doing a keyword search on a popular database like GenBank. The other list might be obtained from the Cancer Genome Anatomy Project (CGAP, Cancer J 7(1)52–60, Schaefer et al, 2001) recommendations and the third maybe the genes she feels play a role in cancer. These three lists if combined manually by the researcher might contain a lot of different gene identifiers representing the same gene. She then manually needs to eliminate such duplicates by searching for each gene. ARROGANT automates this process by allowing only one gene per UniGene cluster, see FIG. 30.

Figure 31A:
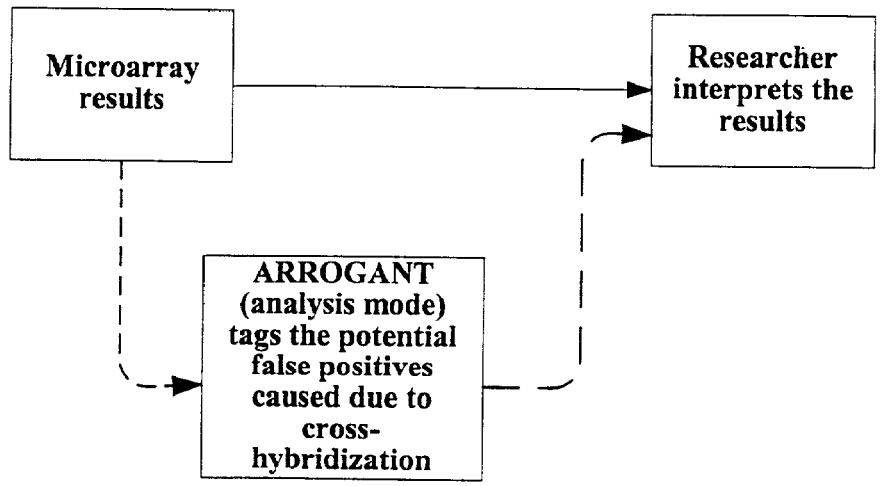
FIGS. 31a–b: ARROGANT tags false-positives
Figure 31B:
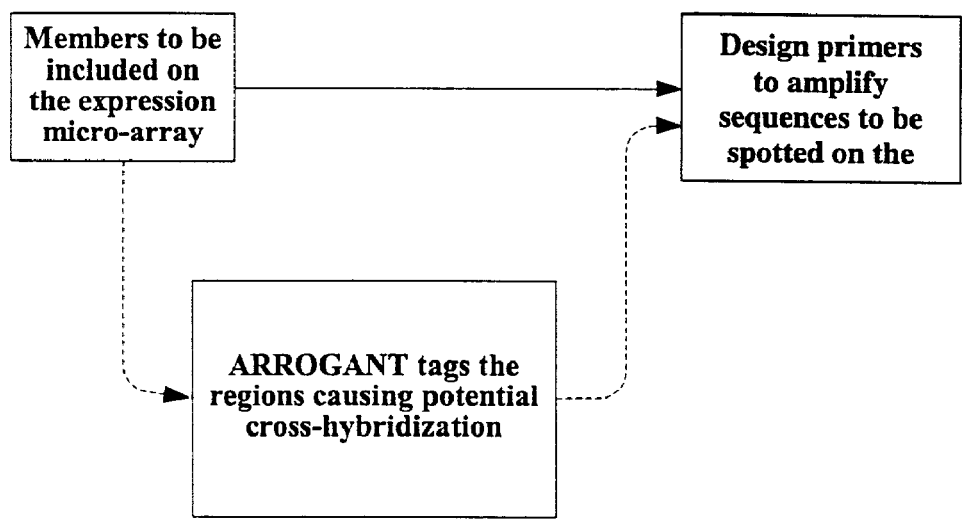

5.7 Cross-Hybridization Analysis: As described earlier ARROGANT estimates the amount of cross-hybridizing signal for each element on the array and tags the potential false positives. FIGS. 31a–b shows the use of ARROGANT to design expression microarrays. ARROGANT can be used to determine the regions that might cause cross hybridization and the researcher could design primers so as to exclude these regions which could have lead to false positives. ARROGANT can be used to tag the potential false positives due to cross hybridization. This helps the researcher in interpreting the expression data in a more thorough manner.

5.8 Search using SQL: Reseachers can directly use various simple SQL queries to retrieve information from many different databases simultaneously. Also conversions like getting gene names for given accession numbers or accession numbers for given descriptions can be achieved using simple SQL queries. For example, using a single SQL query, LocusLink identifiers for all the 15,000 gene names in a collection can be achieved.

Section 6: Results and Validation.

ARROGANT was used for a variety of different applications, including cancer studies, and clones were ordered based on the analysis done by ARROGANT. ARROGANT's ability to estimate potential cross-hybridization was tested on our human array containing 10,000 elements and the cross-hybridizing candidates were categorized as either ALUs, simple sequence repeats or others. ARROGANT was used to recommend new genes for the Program for Genomic Application (PGA) and also used to annotate the existing genes on PGA. ARROGANT identified new genes for studies of Robert's Syndrome and annotated the associated gene list. The analysis mode of ARROGANT was used to annotate several different gene lists which included genes on commercial microarrays (Affymetrix, Inc.), and genes on our 10,000 human array and 12,000 mouse array. These and other applications using databases developed with ARROGANT are discussed below.

6.1 ARROGANT used in cancer studies to recommend candidate genes, look for clones and determine the ones needed to be ordered: The utility of ARROGANT was demonstrated using all its three modes of operation to develop a new human microarray for cancer. Starting with the keyword search feature in the design mode, ARROGANT was used to compile a list of candidate genes for cancer. This list and two more lists obtained from separate sources were then combined to obtain a unique list using the merging gene collection mode. The genes already present on our human microarray (consisting of 10,000 genes) were then eliminated from the list. Now using the analysis mode, clones commercially available with Research Genetics were determined for the ones that needed to be ordered. ARROGANT was later used to verify the insert sizes of the clones obtained from Research Genetics.

6.1.1 Keyword search to obtain possible candidate genes: The keyword search feature of ARROGANT was used to compile a collection of genes possibly associated with cancer using keywords like cancer, metastasis, carcinoma, etc. Collections of 359 probable candidate genes were selected. Now the Analysis mode was used to determine the UniGene clusters for this list of 359 genes to obtain a set of 237 non-redundant genes.

6.1.2 Merging Gene Collection Mode: For a more complete coverage of candidate genes it was decided to merge the list obtained from ARROGANT with 2 more important collections from separate sources. These included 750 genes obtained from experts and another list of 13,969 genes from the CGAP website. The merging gene collection mode was used to compile one unique list of genes by avoiding sequence redundancies. The sequence redundancies were eliminated by having one gene per UniGene cluster. The merge list was compared to our human 10,000 microarray to determine the ones needed to be ordered. It was found that 9,315 genes were not in common with our human 10,000 microarray.

6.1.3 Look for commercially available clones with research genetics: Clones were found with research genetics for 7,593 out of 9,315 genes needed to be ordered. The clones included both sequence verified and non-verified. The results were found to be identical when compared to the output obtained from Research Genetics software program CMiner to look for commercially available clones. The 7,593 clones were ordered.

6.1.4 Verification of clones obtained by determining their insert size: Once the clones were obtained from Research Genetics it was required to verify their insert sizes. The insert sizes can be determined only for the sequence verified clones as obtained from the Research Genetics database. There were 5,739 sequence verified clones out of the 7,593 clones received. ARROGANT could determine the insert sizes for 3,726 clones, as Research Genetics does not provide the insert sizes for all the sequence verified clones.

6.2 Cross-hybridization analysis of the human array containing 10,000 elements. The results obtained from the experiments performed on yeast microarrays suggested that the threshold for a sequence to cross hybridize was an overlap consisting of 65 contiguous hydrogen bonds. ARROGANT was used to further study the effects of cross hybridization using human microarrays. Each gene on the 10,000 human microarray was BLASTed against the rest of the genes on the microarray. The BLAST results were used to find the potential cross-hybridization of each gene with the remaining 9,999 elements on the microarray. ARROGANT also determined the sequences having ALU elements in the 3'/5'/coding region. Table 6.2 gives the distribution of the ALU elements.

TABLE 6.2

Distribution of ALU elements on our human 10,000 microarray.

| Type | 3' | Coding | 5' |
|---|---|---|---|
| ALU | 433 | 0 | 199 |

There are a significant number of ALU elements in the 3' region. Most of the top candidate genes for cross-hybridization were found to contain ALU elements. The significant number of ALU elements in the 3' region suggests that there might be significant amount of cross-hybridization. ARROGANT calculates potential cross-hybridization of each element by sequences within the chip as well as the entire UniGene database.

6.3 ARROGANT used for identifying and annotating genes for polymorphism discovery to link to cardiac diseases for PGA: The Program for Genomic Application (PGA) is a nationwide attempt to use genotnic and proteomic methods to study and investigate cellular responses to injury and inflammation. The program endeavors to identify the genes and proteins involved in these responses. ARROGANT was used to both recommend new candidate genes for PGA as well as annotate the current PGA list of 253 genes. The ability of ARROGANT to find potential candidates was tested by comparing fire list obtained using keyword search with the current list of genes. The list of keywords compiled by researchers participating in PGA was as follows:

| | |
|---|---|
| hyperlipidemia | arteriosclerosis |
| low density lipoproteins | cholesterol |
| dietary responsiveness | inflammation |
| high density lipoproteins | cytokine |
| coronary calcification | orphan receptor |
| insulin resistance | cardiac failure |
| cardiac hypertrophy | signal transduction |
| coronary artery disease | G-protein |
| coronary atherosclerosis | |

ARROGANT found 3,789 genes associated with the above keywords. There were 13 genes found in common with the current PGA list of 253 genes. This demonstrated the keyword search capability of ARROGANT to look for potential candidates associated with keywords. The newly compiled list was annotated using the analysis mode and is available on the web at: <http://ARROGANT.swmed.edu/myweb/hideandsort.asp?txtarray=40710>. ARROGANT was also used to annotate the current PGA list of 253 genes.

The ability of ARROGANT in the analysis mode to accept a list of genes tab delimited with a number was used to assign priority levels to the genes: 2-Highest priority, 1-Moderate priority and 0-Low priority. The annotated table is available on the web at: <http://ARROGANT.swmed.edu/myweb/hideandsort.asp?txtarray=44082>.

6.4 ARROGANT used in the study of Robert's Syndrome: Robert's Syndrome is a genetic disorder caused by chromosome damage during cell division, and characterized by loss of limb bones, cleft palate, heart defects and abnormalities of the abdominal organs. ARROGANT was used to find new potential candidate genes for Robert's syndrome using keywords:

| | |
|---|---|
| Robert syndrome | hypoplastic nasal and auricular cartilage |
| Roberts syndrome | atrial septal defect |
| Robert's syndrome | patent ductus arteriosus |
| Pseudothalidomide syndrome | polycystic kidneys |
| SC phocomelia syndrome | fused kidneys |
| heterochromatin | horseshoe kidneys |
| Heterochromatic repulsion | micronucleation |
| Heterochromatic splaying | enlargement of the phallus |
| Premature centromere separation | absent nails |
| premature separation | ICF syndrome |
| Tetraphocomelia | Centromeric instability immunodeficiency |
| Limb reduction | syndrome |
| hypoplastic | MECP2 |
| Long bone | Methyl binding protein |
| Aneuploidy | Hypomethylation |
| Craniofacial | Hypermethylation |
| Oxycephalic | Demethylation |
| aplasia of the fibula | demethyltransferase |
| bilateral clubfoot | Methylation |
| absence of radii | methylase |
| cleft lip and palate | mSIN3A |

-continued

| | |
|---|---|
| oligodactyly | Histone |
| microcephaly | Histone acetylation |
| exophthalmus | Histone acetylase |
| hypertelorism | Histone deacetylase |
| corneal clouding | TAR syndrome |
| hemangiomas | |

ARROGANT found 6,326 genes, which were further annotated using the analysis mode. The results are available on the web at: <http://ARROGANT.swmed.edu/myweb/hideandsort.asp?txtarray=12345>. A separate list of 16 gene names found to be important in the study of Robert Syndrome was obtained. The accession numbers for these 16 genes were determined using ARROGANT. It was found that there was one gene in common between the two lists. This again demonstrated the utility of ARROGANT to look for and identify candidate genes associated with keywords. The list of 16 genes was also annotated using the analysis mode and the results are available on the web at <http://ARROGANT.swmed.edu/myweb/hideandsort.asp?txtarray=39613=.

6.5 ARROGANT used to annotate genes on commercial DNA chips: ARROGANT was used in the analysis mode to annotate various microarrays available from Affymetrix (Santa Clara, Calif.) to help the researcher view the results obtained from the expression studies in a convenient manner. This provides the researcher a group of genes having particular characteristics together and helps in making important observations. The following commercial (Affymetrix) human and mouse microarrays were analyzed.

1. Human HUG95 microarray: This microarray consists of 12,454 different elements. The annotated list is available on the web at <http://ARROGANT.swmed.edu/myweb/hideandsort.asp?txtarray=11111>.

2. Rat RG-U34 microarray: This consists of 1,322 genes from Rat genome. The results are available on the web at >http://ARROGANT.swmed.edu/myweb/hideandsort.asp?txtarray=57860>.

6.6 ARROGANT used to annotate genes on chromosome 3p: ARROGANT was used to identify genes commonly mutated or whose expression is deregulated in human lung and breast cancers. Although several regions of loss occur on multiple chromosomes it was observed that allele loss in the chromosome 3p21.3 area was the earliest pre-malignant change so far detected in lung cancer development (<http://www.utsouthwestern.edu/cancer/Research/3p21intro.htm>). ARROGANT was used to annotate the 32 genes on chromosome 3p thought to be important in causing lung cancer. The results are available at: <http://ARROGANT.swmed.edu/myweb/hideandsort.asp?txtarray=40357>.

6.7 ARROGANT used to analyze human microarrays: Our laboratory has developed a human cDNA microarray, which consists of 10,000 clones from Research Genetics. Many laboratories in UTSW (University of Texas Southwestern Medical Center at Dallas) are using this microarray for various research studies like cancer, aging, etc. ARROGANT provides annotation for all the genes as one table. The researchers can overlay their expression level data on this table, which would help them make important observations. For example, the researcher could look at the pathways for all the highly expressed genes and also know their position in the genome. Further the researcher could also sort the data using ARROGANT to bring the interesting genes on top of the table. ARROGANT annotation of the human 10,000 array is available on the web at <http://ARROGANT.swmed.edu/myweb/hideandsort.asp?txtarray=60110>. ARROGANT also annotated our earlier human array consisting of 4,200 elements and the results are available at <http://ARROGANT.swmed.edu/myweb/hideandsort.asp?txtarray=60718>.

6.8 Other Applications developed writing simple SQL queries: Due to the implementation of various databases locally in a relational database format, certain features from across databases can be easily retrieved by writing simple SQL queries. ARROGANT has been used for many such applications including:

1. Genomic entries and LocusLink: identifiers for 793 gene names were required. LocusLink identifiers were first retrieved for each of the gene names and genomic entries for each of the LocusLink identifiers were retrieved. This was possible by writing single SQL query since all the databases were implemented locally and stored in the relational database format.

2. Another application required finding pathways for 521 genes having GenBank Numeric Identifiers (NID). Pathway information for each of the 521 genes was retrieved by writing an SQL script using ARROGANT database.

From the above discussion it is seen that ARROGANT can be used in a variety of different applications ranging from annotating any list of genes, recommending new potential candidates associated with keywords to merging different lists of genes to obtain one collection without redundancies.

Section 7: Enhancements and Add-Ons.

ARROGANT has been applied to a variety of different applications as demonstrated in the earlier section and has proved to be a worthy tool. It compiles, annotates and merges large gene collections as well as helps in the design of expression/resequencing microarrays. The following optional features and add-ons enhance its ability to work with large gene collections and improve its ability as a design and analysis tool for microarrays.

1. Include more databases: ARROGANT uses multiple databases in a modular format and makes it convenient to add more databases. Parsers may be used to add more databases like Swissprot and Pfam, to increase the annotating capability of ARROGANT for large gene collections. Additional clone databases, such as proprietary databases (e.g. LifeSeq, Incyte Genomics) enhance the ability of ARROGANT to look for commercial clones, and the addition of literature databases like Medline (NCBI) increase the value of ARROGANT to look for potential candidates by keyword search.

2. Ability to find introns/exon boundaries: ARROGANT can implement programs like GENSCAN (Burge et al, J. Mol. Biol. 1997) to detect introns/exon boundaries for a given gene sequence, enabling the tool to detect possible splice variants and design primers to amplify each exon.

3. Clustering based on pathways: Basic ARROGANT has the capability of sorting the final annotated table (analysis mode) based on pathways. This program is enhanced to use pathway information to cluster together up-regulating/down-regulating elements on the array for each individual pathway.

4. Include keyword search within analysis mode: The user could use the analysis mode to annotate a large gene collection and then use the keyword search within the analysis mode to display only those genes related to a certain keyword. For example, the researcher would want to know the genes associated (by keywords) with cancer from the ones over-expressed in a given microarray experiment. This could be achieved by letting the researcher type in the keywords to be searched and writing a function to look for those keywords within the current annotation table of the analysis mode.

5. Integrate ARROGANT with other processes: Basic ARROGANT uses other laboratory tools like cross-hybridization (to estimate amount of false signal obtained due to genes having significant sequence similarity) and Rep-X (to find potentially polymorphic repeats). The output of more tools like SNIDE which may be used to predict candidate SNPs (Single Nucleotide Polymorphism), may be added as a column to the annotation table of the analysis mode, i.e. adding the output of SNIDE as a table in the ARROGANT database.

6. Use of English query language: SQL Server 7.0 can be trained to enable the users (having direct access to the database) to type queries in simple English language instead of SQL (Structured Query Language). For example SQL server 7.0 software can be trained so that the user could type in queries like 'Give me genes related to cancer but not aging' instead of writing a query programmatically in SQL 7. Include expression level data for more than one experiment in the analysis mode: ARROGANT can also be made to provide basic statistical results e.g. mean, max, etc. along with other annotation. This is to say that expression data from more than one experiment may be included in the same annotation table and columns giving the mean, max and median can be added. In this case ARROGANT directly inputs gene collection, tab delimited by one or more expression level data, and the program automatically determines number of experiments by counting the tabs between each expression data provided.

8. Enhance keyword search: Basic ARROGANT keyword search can be used with two Boolean operators 'AND/OR'. The keyword search capability can be further extended to include more boolean operators like NOT, BUT etc. e.g. 'Aging NOT telomerase' which would translate to look for genes associated with aging but not with telomerase.

9. Basic ARROGANT accepts accession numbers as input identifiers; enhancements provide for accepting gene sequences using various identifiers e.g. GenBank NID, UniGene cluster ID, gene names and LocusLink ID.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A computer-based system for creating from one or more datasets a data table comprising sequence identifiers corresponding to a targeted collection of sequences, the one or more datasets comprising sequence identifiers corresponding to biopolymer sequences and linked to corresponding annotations, the system comprising:
   a) a search function which searches the annotations of the one or more datasets according to one or more user-defined criteria and outputs a first subset of the one or more datasets restricted by the one or more criteria;
   b) a redundancy reducing function which compares the first subset with one or more first databases correlating the sequence identifiers of the first subset with common source gene biopolymers and outputs a second subset of the dataset having reduced biopolymer redundancy relative to the first subset;
   c) a selection function which applies to the second subset a user-defined selection parameter and outputs a third subset of the one or more datasets restricted relative to the second subset by the parameter; and
   d) a tabulation function which creates and outputs the targeted collection of sequences in the form of a data table comprising, configurable by and sortable by the sequence identifiers of the third subset.

2. A system according to claim 1, wherein the one or more criteria is selected from the group consisting of a keyword and a concept.

3. A system according to claim 1, wherein the one or more criteria is one of a plurality of user-defined criteria, and the search function searches the annotations of the one or more datasets according to the one or more criteria and outputs a first subset of the one or more datasets restricted by the one or more criteria.

4. A system according to claim 1, wherein the one or more criteria is one of a plurality of user-defined criteria, and the search function searches the annotations of the one or more datasets according to the one or more criteria and outputs a first subset of the one or more datasets restricted by the one or more criteria, wherein the one or more criteria include multiple keywords.

5. A system according to claim 1, wherein the one or more datasets is one of a plurality of datasets, and the search function searches the annotations of the one or more datasets according to the one or more user-defined criteria and outputs a first subset of the one or more datasets restricted by the one or more criteria.

6. A system according to claim 1, wherein the one or more first databases is one of a plurality of databases correlating the sequence identifiers of the first subset with common source gene biopolymers, and the redundancy reducing function compares the first subset with the one or more first databases and outputs the second subset of the one or more datasets.

7. A system according to claim 1, wherein the parameter is selected from the group consisting of source, species, author, and pathway.

8. A system according to claim 1, wherein the parameter is one of a plurality of user-defined selection parameters, and the selection function applies to the second subset the parameters and outputs the third subset restricted relative to the second subset by the parameters.

9. A system according to claim 1, wherein the redundancy reducing function outputs a second subset of the one or more datasets which eliminates biopolymer redundancy relative to the first subset.

10. A system according to claim 1, further comprising an expansion function which searches a second database for synonyms of the sequence identifiers of the first, second or third subset.

11. A computer-based method for creating from a dataset a data table comprising sequence identifiers corresponding to a targeted collection of sequences the dataset comprising sequence identifiers corresponding to biopolymer sequences and linked to corresponding annotations, the method comprising computer-implemented steps of:
   a) searching with a computer the annotations of the dataset according to a user-defined criterion and outputting a first subset of the dataset restricted by the criterion;
   b) comparing with the computer the first subset with a database correlating the sequence identifiers of the first subset with common source gene biopolymers and outputting a second subset of the dataset having reduced biopolymer redundancy relative to the first subset;

c) applying to the second subset a user-defined selection parameter and outputting a third subset of the dataset restricted relative to the second subset by the parameter; and d) creating and outputting the targeted collection of sequences in the form of a data table comprising, configurable by and sortable by the sequence identifiers of the third subset.

12. A computer-based system for creating from a plurality of datasets a data table comprising sequence identifiers corresponding to a targeted collection of sequences, the datasets comprising sequence identifiers corresponding to biopolymer sequences, the system comprising:

a) a merge and redundancy reducing function which compares the datasets with a database correlating the sequence identifiers with common source gene biopolymers and creates a subset of the sum of the datasets having reduced biopolymer redundancy relative to the sum; and b) a tabulation function which creates and outputs the targeted collection of sequences in the form of a data table comprising, configurable by and sortable by the sequence identifiers of the subset.

13. A system according to claim 12, wherein the merge and redundancy reducing function further comprises a selection function which applies a user-defined selection parameter whereby the subset is restricted relative to the sum of the datasets by the parameter.

14. A system according to claim 12, wherein the merge and redundancy reducing function further comprises a selection function which applies a user-defined selection parameter whereby the subset is restricted relative to the sum of the datasets by the parameter, wherein the parameter is selected from the group consisting of source, author, and pathway.

15. A computer-based method for creating from a plurality of datasets a data table comprising sequence identifiers corresponding to a targeted collection of sequences, the datasets comprising sequence identifiers corresponding to biopolymer sequences, the method comprising computer-implemented steps of:

a) comparing the datasets with a database correlating the sequence identifiers with common source gene biopolymers and creating a subset of the sum of the datasets having reduced biopolymer redundancy relative to the sum; and b) creating and outputting the targeted collection of sequences in the form of a data table comprising, configurable by and sortable by the sequence identifiers of the subset.

16. A computer-based system for creating from a dataset a data table comprising sequence identifiers corresponding to a targeted collection of sequences, the dataset comprising sequence identifiers corresponding to biopolymer sequences and linked to corresponding first annotations, the system comprising:

a) an integration function which merges the dataset with a database comprising second annotations attributable to and correlated with at least a subset of the sequence identifiers or sequences of the dataset and which links the second annotations to the corresponding sequence identifiers of the subset; and b) a tabulation function which creates and outputs the targeted collection of sequences in the form of a data table comprising, configurable by and sortable by the sequence identifiers of the subset and the second annotations.

17. A system according to claim 16, wherein the second annotations comprise data attributable to and correlated with at least a subset of the sequence identifiers or sequences of the dataset, said data selected from the group consisting of gene expression data, sequencing data, genotype data, polymorphism data and clinical data.

18. A computer-based method for creating from a dataset a data table comprising sequence identifiers corresponding to a targeted collection of sequences, the dataset comprising sequence identifiers corresponding to biopolymer sequences and linked to corresponding first annotations, the method comprising computer-implemented steps of:

a) merging the dataset with a database comprising second annotations attributable to and correlated with at least a subset of the sequence identifiers or sequences of the dataset and linking the second annotations to the corresponding sequence identifiers of the subset; and b) creating and outputting the targeted collection of sequences in the form of a data table comprising, configurable by and sortable by the sequence identifiers of the subset and the second annotations.

19. A system according to claim 1, further comprising:

a second computer-based system for creating from a plurality of datasets a data table comprising sequence identifiers corresponding to a targeted collection of sequences, the datasets comprising sequence identifiers corresponding to biopolymer sequences, the second system comprising:

a) a merge and redundancy reducing function which compares the datasets with a database correlating the sequence identifiers with common source gene biopolymers and creates a subset of the sum of the datasets having reduced biopolymer redundancy relative to the sum; and b) a tabulation function which creates and outputs the targeted collection of sequences in the form of a data table comprising, configurable by and sortable by the sequence identifiers of the subset.

20. A system according to claim 1, further comprising:

a second computer-based system for creating from a dataset a data table comprising sequence identifiers corresponding to a targeted collection of sequences, the dataset comprising sequence identifiers corresponding to biopolymer sequences and linked to corresponding first annotations, the second system comprising:

a) an integration function which merges the dataset with a database comprising second annotations attributable to and correlated with at least a subset of the sequence identifiers or sequences of the dataset and which links the second annotations to the corresponding sequence identifiers of the subset; and b) a tabulation function which creates and outputs the targeted collection of sequences in the form of a data table comprising, configurable by and sortable by the sequence identifiers of the subset and the second annotations.

21. A system according to claim 1, further comprising:

a second computer-based system for creating from a plurality of datasets a data table comprising sequence identifiers corresponding to a targeted collection of sequences, the datasets comprising sequence identifiers corresponding to biopolymer sequences, the second system comprising:

a) a merge and redundancy reducing function which compares the datasets with a database correlating the sequence identifiers with common source gene biopolymers and creates a subset of the sum of the datasets having reduced biopolymer redundancy relative to the sum; and b) a tabulation function which creates and outputs the targeted collection of sequences in the form of a data table comprising, configurable by and sortable by the sequence identifiers of the subset; and, a third computer-based system for creating a targeted collection of sequences from a dataset comprising sequence identifiers corresponding to biopolymer sequences and linked to corresponding first annotations, the third system comprising:

a) an integration function which merges the dataset with a database comprising second annotations attributable to and correlated with at least a subset of the sequence identifiers or sequences of the dataset and which links the second annotations to the corresponding sequence identifiers of the subset; and b) a tabulation function which creates and outputs the targeted collection of sequences in the form of a data table comprising, configurable by and sortable by the sequence identifiers of the subset and the second annotations.

* * * * *